(12) United States Patent
Jin et al.

(10) Patent No.: US 8,127,839 B2
(45) Date of Patent: *Mar. 6, 2012

(54) FORMATION PRETREATMENT WITH BIOGENIC METHANE PRODUCTION ENHANCEMENT SYSTEMS

(75) Inventors: Song Jin, Fort Collins, CO (US); Alan E. Bland, Laramie, WY (US)

(73) Assignee: University of Wyoming Research Corporation, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/901,169

(22) Filed: Oct. 8, 2010

(65) Prior Publication Data

US 2011/0027849 A1   Feb. 3, 2011

Related U.S. Application Data

(63) Continuation of application No. 11/990,417, filed as application No. PCT/US2006/031723 on Aug. 14, 2006, now Pat. No. 7,832,475.

(60) Provisional application No. 60/707,697, filed on Aug. 12, 2005.

(51) Int. Cl.
*E21B 43/22* (2006.01)
*C12P 5/02* (2006.01)

(52) U.S. Cl. .................. 166/246; 166/371; 435/167
(58) Field of Classification Search .................. None
See application file for complete search history.

(56) References Cited

U.S. PATENT DOCUMENTS

| | | | |
|---|---|---|---|
| 3,640,846 A | 2/1972 | Johnson | |
| 3,826,308 A | 7/1974 | Compere-Whitney | |
| 4,151,068 A | 4/1979 | McCollum et al. | |
| 4,358,537 A | 11/1982 | Chynoweth | |
| 4,826,769 A | 5/1989 | Menger | |
| 4,845,034 A | 7/1989 | Menger et al. | |
| 4,883,753 A | 11/1989 | Belaich et al. | |
| 5,340,376 A | 8/1994 | Cunningham | |
| 5,350,684 A | 9/1994 | Nakatsugawa et al. | |
| 5,424,195 A | 6/1995 | Volkwein | |
| 5,494,108 A | 2/1996 | Palmer et al. | |
| 5,566,756 A | 10/1996 | Chaback et al. | |
| 5,670,345 A | 9/1997 | Srivastava et al. | |
| 5,919,696 A | 7/1999 | Ikeda et al. | |
| 6,090,593 A | 7/2000 | Fleming et al. | |

(Continued)

FOREIGN PATENT DOCUMENTS

| | | |
|---|---|---|
| WO | 79/00201 | 4/1979 |
| WO | 94/25730 | 10/1994 |
| WO | 01/68904 A1 | 9/2001 |
| WO | 2004/003506 A2 | 1/2004 |
| WO | 2007/022122 A2 | 2/2007 |

OTHER PUBLICATIONS

International Application No. PCT/US06/31723; International Search Report dated Jul. 31, 2007.

(Continued)

*Primary Examiner* — Zakiya W Bates
(74) *Attorney, Agent, or Firm* — Santangelo Law Offices, P.C.

(57) ABSTRACT

Systems for enhanced in-situ or perhaps even ex-situ biogenic methane production from hydrocarbon-bearing formations (1) including coal seam, oil shale, coal, coal derivates and the like are presented in embodiments such as but not limited to: increasing and perhaps even selection of microbial populations (2), amending CBM water and other microbe-containing media, diminishing sulfate reduction competition, enhancing organic matter concentrations and generation of biogenic methane (10), universally treating hydrocarbon-bearing formations, and introducing amendments (3) to hydrocarbon-bearing formations.

31 Claims, 21 Drawing Sheets

U.S. PATENT DOCUMENTS

| | | | |
|---|---|---|---|
| 6,210,955 | B1 | 4/2001 | Hayes |
| 6,543,535 | B2 | 4/2003 | Converse et al. |
| 6,571,874 | B1 | 6/2003 | Lovenich et al. |
| 2004/0033557 | A1 | 2/2004 | Scott et al. |
| 2004/0200618 | A1 | 10/2004 | Piekenbrock |
| 2005/0061001 | A1 | 3/2005 | Maston |
| 2005/0082058 | A1 | 4/2005 | Bustin et al. |
| 2007/0248531 | A1 | 10/2007 | Debryun et al. |
| 2009/0023612 | A1* | 1/2009 | Pfeiffer et al. ............... 507/201 |

OTHER PUBLICATIONS

International Application No. PCT/US06/31723; Written Opinion of the International Searching Authority dated Jul. 31, 2007.

International Application No. PCT/US06/31723; International Preliminary Report on Patentability dated Feb. 22, 2008.

Parent Application—U.S. Appl. No. 11/990,417, filed Feb. 12, 2008.

Parallel Australia application serial No. 200679679 filed Feb. 13, 2008; Notice of Allowance dated Jul. 25, 2011.

* cited by examiner

FORMATION PRETREATMENT WITH BIOGENIC METHANE PRODUCTION ENHANCEMENT SYSTEMS

This application is a continuation of application Ser. No. 11/990,417 filed Feb. 12, 2008 which is the United States National Stage of international application number PCT/2006/031723 filed Aug. 14, 2006 which claims the benefit of U.S. Provisional Application No. 60/707,697 filed Aug. 12, 2005, each hereby incorporated by reference herein. Any priority case is hereby incorporated by reference herein.

ACKNOWLEDGMENT OF GOVERNMENT SUPPORT

This technology relates to work performed under U.S. DOE Cooperative Agreement #DE-FC26-98FT40322. The U.S. government may have certain rights in this inventive technology, including "march-in" rights, as provided for by the terms of U.S. DOE Cooperative Agreement #DE-FC26-98FT40322.

TECHNICAL FIELD

The present invention relates to biogenic production of methane in ex-situ and even in-situ systems. Specifically, embodiments may provide various kinds of amendments such as but not limited to microbial population stimulation amendments, indiscriminate microbial population stimulation amendments, additional microbial population stimulation amendments, sulfate reduction competition shield amendments, predetermined microbial population stimulation amendments, and the like which can be introduced into various hydrocarbon-bearing formations to enhance the production of biogenic methane.

BACKGROUND OF THE INVENTION

Methane may be mainly formed through thermogenic and methanogenic (biogenic) processes. Biogenic methane may be believed to consist of about 20-40% of the total methane storage on earth, and higher ratios (such as about 65%) under favorable bio-geological conditions. Methanogens may be strictly anaerobic archaebacteria. Biogenic methane production may be carried out by methanogens through methanogenesis, in which carbon dioxide and small organic molecules may be converted to methane through a series of biological reactions perhaps by microbial populations as those skilled in the art can appreciate. Isotope fractionation studies may have verified that biogenic methane is actively produced in coal seam and oil shale and the like, which may contain a rich source of small organic compounds to serve as substrates for methanogenesis. Accordingly, methanogenesis can produce methane from oil shale, coal, coal derivatives, lignite, and the like by removing hydrogen and carbon from a source.

Methane production processes may be a versatile biotechnology capable of converting almost all types of polymeric materials to methane and carbon dioxide under anaerobic conditions. This may be achieved as a result of the consecutive biochemical breakdown of polymers to methane and carbon dioxide in an environment in which a variety of microorganisms which may include fermentative microbes (acidogens); hydrogen-producing, acetate-forming microbes (acetogens); and methane-producing microbes (methanogens) harmoniously grow and produce reduced end-products. Anaerobes may play important roles in establishing a stable environment at various stages of methane production.

Coal bed methane ("CBM"), as an example, may demonstrate that CBM water overlaying coal seam may be able to support observable methane production under anaerobic conditions. Methane production may not have been observed in sterile controls, possibly confirming it may be a microbially mediated process. Indigenous methanogens have been detected as present in the coal cores extracted from the Powder River Basin (PRB), indicating a potential of enhancing the methanogenic activities as an economically feasible approach to harvest bioreservoir of CBM.

Currently, an effective technology to identify and enhance biogenic methane production in coal seam, oil shale, and the like may be lacking. For example, U.S. Pat. No. 6,543,535 to Converse, hereby incorporated by reference, includes analysis of subterranean formations and stimulating activity of microbial consortia based on the analysis in a subterranean formation to convert hydrocarbons to methane. However, applicability of enhancement of biogenic methane production to a wide variety of situations and even efficient enhancement of biogenic methane is desired in the industry.

DISCLOSURE OF THE INVENTION

It is therefore an object of the present invention, in embodiments, to provide an identification of potential methane production sources.

It is yet another object of the present invention, in embodiments, to enhance biogenic methane production from coal seam, oil shale, coal, coal derivatives, lignite, and the like.

It is object of the present invention, in embodiments, to introduce amendments to hydrocarbon-bearing formations perhaps even as in a pre-treatment step to biogenic methane production.

It is yet another object of the present invention, in embodiments, for universal treatment such as with introduction of predetermined amendments to hydrocarbon-bearing formations perhaps even as in a pre-treatment step to biogenic methane production.

It is another object of the present invention, in embodiments, to manipulate parameters that affect the occurrence and rates of methanogenesis in coal seam, oil shale, and the like.

It is yet another object of the present invention, in embodiments, to diminish sulfate reduction competition.

It is another object of the present invention, in embodiments, to starve and perhaps even select capable microbial populations such as methanogens.

It is another object of the present invention, in embodiments, to enhance organic matter release from sources such as coal, coal seam, oil shale and the like.

It is another object of the present invention, in embodiments, to provide ex situ systems and in-situ systems for biological methane production.

It is yet another object of the present invention, in embodiments, to beneficially use recycled water such as coal bed methane water and agriculture wastes containing organic constituents, and the like for methane production.

It is yet another object of the present invention, in embodiments, to degrade hydrocarbon and other organic components during or perhaps even after the operations of exploring and extracting oil shale, coal, lignite and the like. The components, for example, may be residual oil remained in oil shale or produced water, residual organic compounds in coal or produced water.

Naturally, further objects, goals and embodiments of the inventions are disclosed throughout other areas of the specification.

MODE(S) FOR CARRYING OUT THE INVENTION

Figure 1:
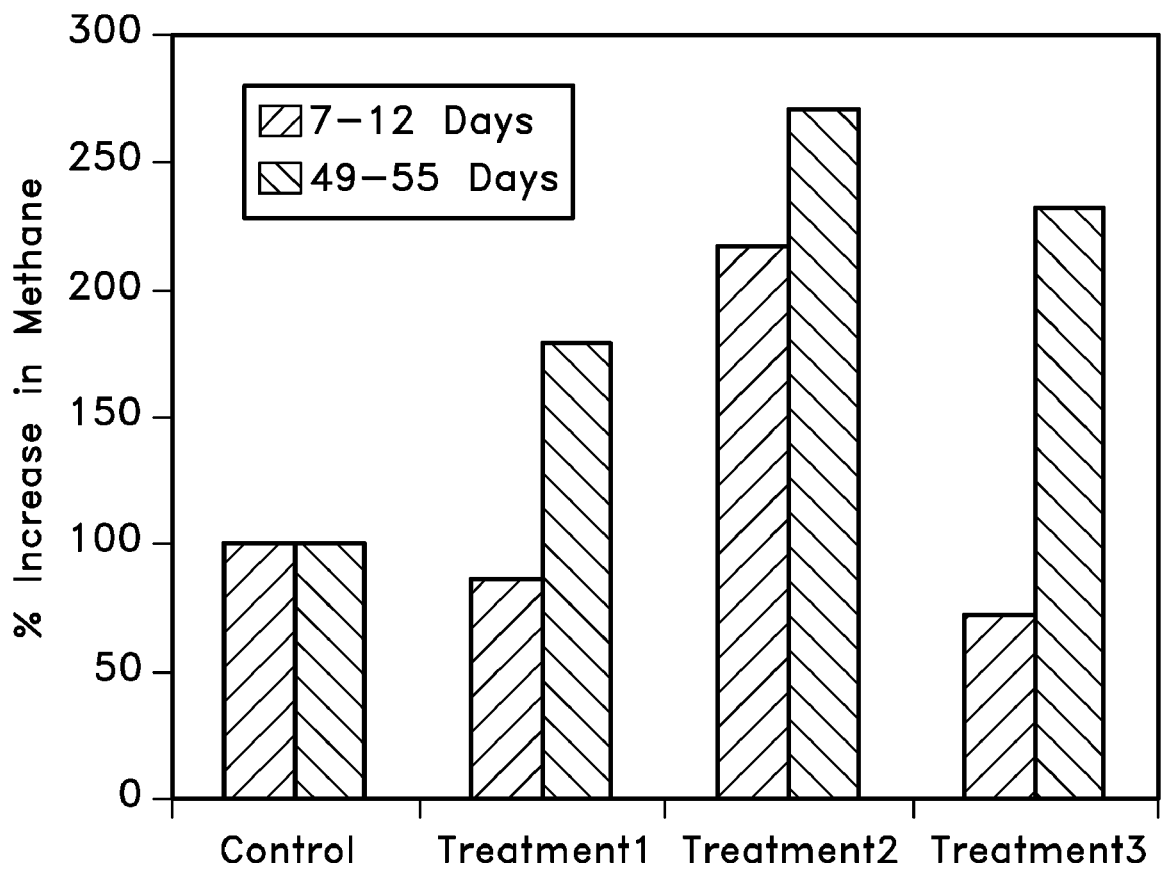
FIG. 1 shows an example of data from treatments on oil shale and the percentage of increase in methane in accordance with some embodiments of the present invention.

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

This present invention includes several embodiments in in-situ and ex-situ enhancing of biogenic methane production from coal seam, oil shale, coal, waste coal, coal derivatives, peat, lignite, oil formations, petroleum sludge, drill cuttings, tar sands, hydrocarbon-contaminated soil, and the like. In embodiments, the present invention may include an evaluation of biogenic methane reserve in coal seam, oil shale and the like with ex-situ or perhaps even in-situ environments. It may be desirable to provide a two component system to estimate and predict the potential of biogenic methane production: methanogenic population and perhaps substrate bioavailability. Indigenous core samples may be collected from the sites of interest. Core samples may be crushed and extracted properly. Microbial sample preparation and real time Polymerase Chain Reaction ("PCR") may be used to determine the population density of methanogens. Total dissolved organic carbon ("DOC") can be quantified from the core samples. A stoichiometric calculation can be used to predict the amount of methane that can be released from the site. As a non-limiting example, table 1, below, represents a conversion from carbon to methane. Specifically, Table 1 is based on 64 mol of C converted to 49 mol of methane.

TABLE 1

| Carbon Source | mg C/kg | mol C/kg | mol CH4/kg source | g CH4/kg Source | lbs. CH4/ton Source |
| --- | --- | --- | --- | --- | --- |
| Oil Shale | 3865 | 0.322083 | 0.246595052 | 2.959140625 | 6.523721422 |
| Coal | 22.092 | 0.001841 | 0.001409516 | 0.016914188 | 0.037289018 |
| Lignite | 506.94 | 0.042245 | 0.032343828 | 0.388125938 | 0.855662442 |

In embodiments, the present invention may provide methods for enhancement of biogenic methane production and even biogenic methane production systems. It may be desirable to provide a population boost of indigenous methanogens. In some embodiments, the present invention may provide a hydrocarbon-bearing formation perhaps initially having a microbial population perhaps even at least one, at least two or even more microbial populations. Microbial populations may be an indigenous microbial population in that they may have originated or may even occur naturally in an area or environment. For example, a microbial population may have pre-existed with a hydrocarbon-bearing formation. Of course, in other embodiments, a microbial population may be added to a hydrocarbon-bearing formation to enhance methanogenic activities.

In the various embodiments discussed herein, a hydrocarbon-bearing formation or even a hydrocarbon-bearing formation environment may include, but is not limited to, oil shale, coal, coal seam, waste coal, coal derivatives, lignite, peat, oil formations, tar sands, hydrocarbon-contaminated soil, petroleum sludge, drill cuttings, and the like and may even include those conditions or even surroundings in addition to oil shale, coal, coal seam, waste coal, coal derivatives, lignite, peat, oil formations, tar sands, hydrocarbon-contaminated soil, petroleum sludge, drill cuttings, and the like. In some embodiments, the present invention may provide an in-situ hydrocarbon-bearing formation sometimes referred as an in-situ hydrocarbon-bearing formation environment or in-situ methane production environment. Embodiments may include an ex-situ hydrocarbon-bearing formation sometimes referred to as an ex-situ hydrocarbon-bearing formation environment or an ex-situ methane production environment. In-situ may refer to a formation or environment of which hydrocarbon-bearing sources may be in their original source locations, for example, in-situ environments may include a subterranean formation. Ex-situ may refer to formations or environments where a hydrocarbon-bearing formation has been removed from its original location and may perhaps even exist in a bioreactor, ex-situ reactor, pit, above ground structures, and the like situations. As a non-limiting example, a bioreactor may refer to any device or system that supports a biologically active environment.

The present invention may provide, in embodiments, starvation and perhaps even selection of capable methanogens. Upon the population growth of methanogens, initially amended substrates can be depleted within a short period of time. Methanogens can go through a "starvation" period in which an "easy food source" may no longer be available.

A rapid adaptation, genetic mutation, and perhaps even gene transfer through plasmids, transposons and other possible pathways may perhaps selectively enhance the methanogens that can utilize small organic compounds from coal seam, oil shale, and the like. These small organic compounds may preexist or perhaps even originate from the degradation of organic matter in the coal, oil shale, or the like. This may provide an enhanced methane production and may even provide biogenically generated methane derived from a sustained boosted microbial population.

At least one indiscriminate microbial population stimulation amendment may be introduced or perhaps even delivered into a hydrocarbon-bearing formation. Microbial populations may microbially consume at least one indiscriminate microbial population stimulation amendment. As a result of the microbial consumption of at least one indiscriminate microbial population stimulation amendment, a blanket boosting of the microbial populations may occur and may provide at least some boosted microbial populations. This may provide an increase of perhaps all of the microbial populations. As the microbes consume the amendments, microbial depletion of at least one indiscriminate microbial population stimulation amendment may result. Accordingly, at least one of the boosted microbial populations may begin to starve and thus providing at least one starved microbial population. Only those microbial populations which can survive on the remaining amendments, organic matter created, and perhaps even the hydrocarbon-bearing formation amendments may survive. As a result, a selective reduction of any starved, boosted microbial population(s) may occur. Conversely, embodiments may provide for selectively sustained at least one sustained, boosted microbial population. Boosted microbial population(s) may then be stimulated to microbially convert hydrocarbons to methane.

As discussed in the various embodiments herein, stimulating at least one microbial population with at least one amendment may include increasing organic matter concentrations within a formation or environment and perhaps even feeding at least one microbial population. An introduction of amendments or the like can cause stimulation of microbial populations perhaps to even create a series of metabolic interactions among microbial populations. Introduction of amendments may be referred to as pretreatment in some embodiments. As a result, biogenically generated methane may be derived from a series of metabolic interactions among at least one microbial population.

In embodiments, at least one of the microbial populations may include a methanogen population and accordingly, such selective processes may therefore increase an indigenous methanogenic population. Methanogens may be a main player in methane production. It may be that a higher a population of methanogens may result in a larger production of methane. In embodiments, an indiscriminate microbial population stimulation amendment may include simple or perhaps even easy substrates, such as but not limited to dairy wastes and the like, and may be used to feed a whole microbial community perhaps as a pretreatment step. This may boost up populations in the microbial community such as but not limited to methanogens, the associated bacterial species, for example, fermenters, and the like microbial community populations.

Readily available substrates such as corn syrup, emulsified oil, lactate, fresh or spoiled milk, any combination thereof, and the like may be used as, but is not limited to, an indiscriminate microbial population stimulation amendment which may even be introduced into a hydrocarbon-bearing formation. In other embodiments, an introduction of indiscriminate microbial population stimulation amendments can be combined with a fracturing process as discussed below. Indiscriminate microbial population stimulation amendments may have no selectiveness to microbes. As such, a blanket boost of microbial populations may be expected. Injected substrates can be depleted within short period of time, as they may be preferred by every microbial group. Upon the depletion of the injected substrates, microbes may be exposed to a selection. It may be desirable to discontinue any introduction of any indiscriminate microbial population stimulation amendment to a hydrocarbon-bearing formation so that those injected amendments can be depleted. Only those capable of degrading a hydrocarbon-bearing formation may sustain their metabolism and growth. Other species could be outcompeted due to starvation of at least one of the boosted microbial populations. The end result may provide a chain of microbial pathways. This pathway can degrade a hydrocarbon-bearing formation through intermediates and eventually produce methane. The initial addition of an indiscriminate microbial population stimulation amendment(s) may increase microbial population, therefore generating methane from at least one boosted microbial population and may provide methane produced from microbial conversion of hydrocarbons.

In other embodiments, at least one additional microbial population stimulation amendment may be introduced into a hydrocarbon-bearing formation environment. Such introduced additional microbial population stimulation amendment may be used to further increase methane production by microbial population stimulation. An introduced additional microbial population stimulation amendment may include, but is not limited to, nitrogen, phosphorous, vitamins, organic carbon, biotin, folic acid, pyrodoxine hydrochloride, thiamine hydrochloride, riboflavin, nicotinic acid, DL-calcium panthenate, vitamin B12, p-aminobenzoic acid, lipoic acid, any combination thereof, and the like. In another embodiment, an introduced additional microbial population stimulation amendment may also include, but is not limited to, biowastes, lactate, milk, returned milk, nitrogen, phosphorous, vitamins, salts, micronutrients, surfactants, acids, bases, oxidants, acetic acid, sodium hydroxide, percarbonate, peroxide, sodium carbonate, sodium bicarbonate, hydrated sodium carbonate, any combination thereof and the like.

The present invention may provide in embodiments, a beneficial use of recycled water such as, but not limited to, produced water, groundwater, local groundwater, water from coal bed methane ("CBM"), wastewater, coal produced water, CBM produced water, and any reused water or perhaps even reused liquid. One design of this technology may use recycled water as a carrier to enhance biogenic methane production. It may offer a beneficial use of the water and an innovative method of its disposal. For example, in the CBM case, produced water from a CBM site can be beneficially used as a carrier. Amendments such as substrates (biowastes, lactate, milk, etc.) and perhaps even essential nutrients (nitrogen, phosphorus, vitamins, salts, and other micro nutrients, etc.) can be amended to recycled water. Recycled water carrying an amendment or amendments (the various types of amendments which can be injected are discussed herein) may be injected into a hydrocarbon-bearing formation. Recycled water may even be injected into ex-situ or even in-situ methane production environments. In some embodiments, recycled water may have microbial populations, methanogen populations, or the like existing in the water from a previous treatment. These residing microbes, methanogens or the like may be delivered to a hydrocarbon-bearing formation and may even further enhance biogenic methane production.

For example, an amended produced water may be injected back into the coal seam as those skilled in the art can appreciate. An injection element such as recycled injection amendment, a produced water injection element, a groundwater injection element, or perhaps even a coal bed methane water injection element, and the like may include those elements which allow the addition of an amended water in a hydrocarbon-bearing formation perhaps under pressure, by gravity forces, other water injection methods and elements, and the like as those skilled in the art can appreciate. An amended produced water may assist in exponential growth of a population of methanogens. As a result of the methanogenic activities during this phase, biogenic methane may be generated, and perhaps even amended substrates can serve as a main electron source. Also during this process, other non-methanogenic populations can be increased due to favorable conditions provided by the amendments. For example, some microbial groups may be important in degrading coal seams, coal, coal derivatives, oil shale, and the like and may release small organic compounds that can be amenable to methanogens to produce methane in later stages.

In yet other embodiments, the present invention may provide diminishing sulfate reduction competition in a methane production environment. Sulfate may be a competing process to methanogenesis and sulfide, a product of sulfate reduction, may be toxic to microbial populations such as methanogens. In embodiments, it may be desirable to introduce a sulfate reduction competition shield amendment into a hydrocarbon-bearing formation. A sulfate reduction competition shield amendment may include, but is not limited to, nitrite, ferrous iron, a combination of the two, and the like and may even be delivered to a hydrocarbon-bearing formation environment to perhaps reduce or even eliminate sulfate reduction competition and its products. If a high sulfate concentration may be present in the coal seam, oil shale, coal, coal derivatives, and the like, injected water, injected recycled water, or the like, trace amounts of nitrite and perhaps even a stoichiometric amount of ferrous iron can be introduced as amendments. Nitrite may be an effective inhibitor to sulfate reduction and ferrous iron can bind with sulfide. These "double" shields can eliminate the adverse competition from sulfate reduction and ensure a population growth and activities of methanogens.

In other embodiments, the present invention may include an induction or perhaps even enhancement of organic matter released from coal, oil shale and the like. Physical (e.g., fracture and the like) and chemical approaches (e.g., treating with surfactants, acids, bases, oxidants, such as but not limited to acetic acid, sodium hydroxide, percarbonate, peroxide and the like) can be applied to enhance an availability of organic matters in coal and oil shale. These methods may be used to break down coal, oil shale, lignite, coal derivatives and the like structures to release more organic matters, or perhaps even to make them more vulnerable to be degraded into smaller organic compounds. These organic matters may be consumed by methanogens to create methane.

The present invention may include, in embodiments, methods of ex-situ enhancing biogenic methane production and perhaps even ex-situ biogenic methane production systems. A hydrocarbon-bearing formation (1) may be extracted from a subterranean source (16) as may be represented in FIG. 17B. At least one microbial population (2)—which may include, in embodiments, at least one methanogen population—may be extracted with a hydrocarbon-bearing formation and both may be placed in an ex-situ methane production environment (17). In embodiments and as one example is shown in FIG.

16, an ex-situ methane production environment may include a bioreactor as discussed herein. Introduction of at least one microbial population stimulation amendment to an ex-situ methane production environment (15) may be desired. Such introduced microbial population stimulation amendment may include amendments such as but not limited to, biowastes, lactate, milk, returned milk, nitrogen, phosphorous, vitamins, salts, micronutrients, surfactants, acids, bases, oxidants, acetic acid, sodium hydroxide, percarbonate, peroxide, sodium carbonate, sodium bicarbonate, hydrated sodium carbonate, any combination thereof, and the like. Amendments may provide stimulation of a microbial population(s) as discussed above. Accordingly, biogenically generated methane (32) may be produced in an ex-situ methane production environment as derived from the introduced microbial population stimulation amendment, in various embodiments.

Figure 18:
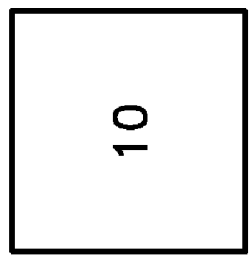
FIG. 18 is a conceptual representation of an introduction of various types of amendments to any kind of hydrocarbon-bearing formation in accordance with some embodiments of the present invention.
Figure 18:
Figure 18:
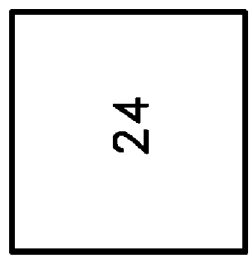
Figure 18:
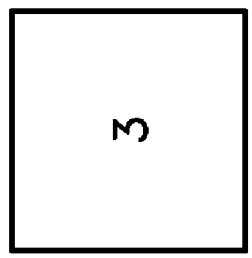
Figure 18:
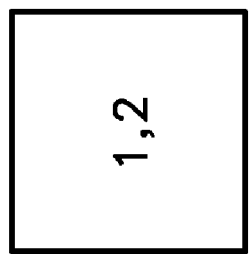

FIG. 18 is a conceptual representation of a hydrocarbon-bearing formation (1) having at least one microbial population (2). In embodiments, a hydrocarbon-bearing formation (1) may be present in an in-situ methane production environment or perhaps even an ex-situ methane production environment. Addition of various types of amendments (3), as herein discussed, may be added to the hydrocarbon-bearing formation (1). Various biogenic processes (24), as herein discussed, may occur and biogenically generated methane (10) may result.

As discussed herein, various embodiments of the present invention may include generating methane from a stimulated microbial population. Accordingly, methane may be generated by microbial conversion of hydrocarbons. Methane can be collected with a methane collection element (11) for further processing. Such methane collection may be obtained by conventional methods as those skilled in the art can appreciate. For example, pressure methods may be used or perhaps even head-space collection methods, and the like can be used for methane collection.

Figure 16:
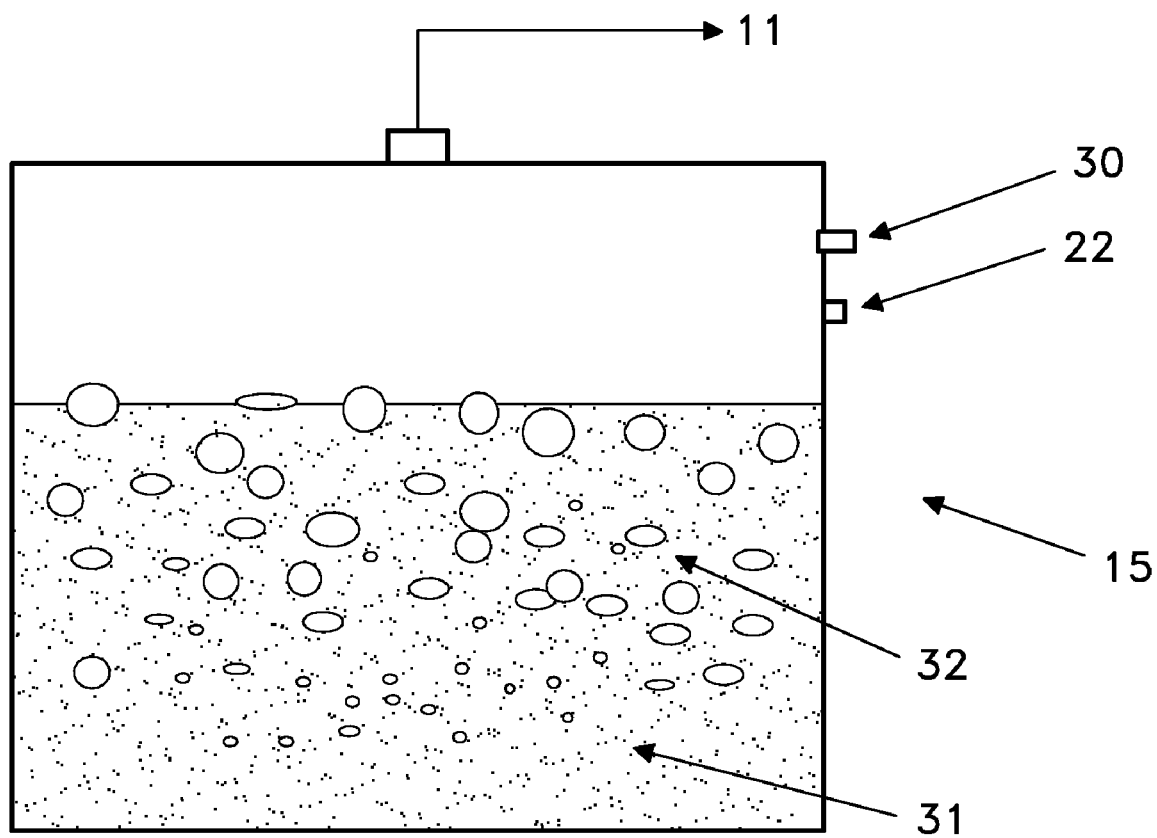
FIG. 16 represents an ex-situ environment for biogenic methane production in accordance with some embodiments of the present invention.

As may be understood in FIG. 16, generally a hydrocarbon-bearing formation (31) may be placed in an ex-situ methane production environment (15). Amendments—a variety of which are discussed herein—may be added to the hydrocarbon-bearing formation through an amendment injection element (22). A sampling port (30) may be included, in embodiments. Biogenically generated methane (32) may be produced and may be collected with a methane collection element (11).

The present invention may provide, in embodiments, methods for universal enhancement of biogenic methane production and even universal biogenic methane production systems. It may be desirable to apply a universal treatment to a hydrocarbon-bearing formation of which the user does not need to do any specific analysis of the formation—perhaps even the exclusion of any analysis of existing microbial populations in the hydrocarbon-bearing formation. This universal treatment may provide a predetermined recipe to apply to a hydrocarbon-bearing formation to allow efficient enhancement of methane production. Such predetermination may include table look up, analysis from pretreatments, laboratory based analysis, and the like.

A hydrocarbon-bearing formation environment perhaps even having at least one microbial population may be provided. In embodiments, the present invention may include an indigenous microbial population which may have pre-existed with a hydrocarbon-bearing formation as further discussed herein. Of course, a hydrocarbon-bearing formation environment may be in an in-situ or perhaps even in an ex-situ environment. At least one predetermined microbial population stimulation amendment may be introduced to a hydrocarbon-bearing formation. For example, a general recipe may be used to convert methane in the subsurface for different materials. These materials may include but are not limited to coal, oil shale, lignite, and the like. An introduced predetermined microbial population stimulation amendment may include but is not limited to, a coal specific predetermined amendment, an oil shale specific predetermined amendment, a lignite specific predetermined amendment, a coal seam specific predetermined amendment, a waste coal specific predetermined amendment, a coal derivative specific predetermined amendment, a peat specific predetermined amendment, an oil formation specific predetermined amendment, a tar sand specific predetermined amendment, a petroleum sludge specific predetermined amendment, a drill cutting specific predetermined amendment, a hydrocarbon-contaminated soil specific predetermined amendment, and the like. Introduction of predetermined microbial population stimulation amendment(s) may occur through injection into a hydrocarbon-bearing formation as herein discussed. The amendments may therefore provide stimulation of the microbial population(s)—such microbial population(s) may include at least one methanogen population, in embodiments—thus generating methane from the stimulated microbial population(s). Again, the methane may be collected as discussed herein.

Generally, a predetermined microbial population stimulation amendment may include ingredients, such as but not limited to, nitrogen, phosphorous, vitamins, organic carbon, biotin, folic acid, pyrodoxine hydrochloride, thiamine hydrochloride, riboflavin, nicotinic acid, DL-calcium panthenate, vitamin B12, p-aminobenzoic acid, liponic acid, any combination thereof, and the like.

Of course other amendments may be introduced, such as but not limited to, biowastes, lactate, milk, returned milk, nitrogen, phosphorous, vitamins, salts, micronutrients, surfactants, acids, bases, oxidants, acetic acid, sodium hydroxide, percarbonate, peroxide, sodium carbonate, sodium bicarbonate, hydrated sodium carbonate, any combination thereof, and the like. These amendments may further enhance biogenic methane production.

In embodiments, it may be desirable to apply a pretreatment to the hydrocarbon-bearing formation, perhaps even to a coal formation, before any addition of predetermined microbial population stimulation amendment(s). This may include the addition of a basic solution to bring the pH to 10. It may be desirable to wait for 24-48 hours and adjust pH down to less than 8 thereafter, in embodiments. The pH may be measured in the overlaying water. In other embodiments, it may be desirable to apply a pretreatment to the hydrocarbon-bearing formation, perhaps even an oil shale formation, before any addition of predetermined microbial population stimulation amendment(s). This may include the addition of a basic solution to lignite to bring pH to 10. It may be desirable to wait for 24-48 hours and adjust pH down to 9 thereafter, in embodiments. In yet other embodiments, instead of basic solution, commercial surfactants can be used for pre-treatment.

The following lists non-limiting examples of various predetermined amendments which can be combined or applied separately and may even be used with in-situ environments. In some instances, a range of +/−30% may be added to the amounts in the following formulas. These are examples only and other predetermined amendments may be used with the various hydrocarbon-bearing formations for enhancement of biogenic methane production.

One example of a coal specific predetermined amendment may include:
- Add 220 g of N per kg of coal (NOTE: calculate the amount of fertilizer based on its N content)
- Add 50 g P per kg of coal (NOTE: calculate the amount of fertilizer based on its P content)
- Add vitamins in the following amounts per kg coal
  - 0.333 g Biotin
  - 0.333 g Folic Acid
  - 1.667 g Pyrodoxine Hydrochloride
  - 0.833 g Thiamine Hydrochloride
  - 0.833 g Riboflavin
  - 0.833 g Nicotinic Acid
  - 0.833 g DL-Calcium Panthenate
  - 0.017 g Vitamin $B_{12}$
  - 0.833 g p-Aminobenzoic Acid
  - 0.833 g Lipoic Acid Another example of a coal specific predetermined amendment may include:
- Add 625 g of organic C per kg coal to increase methanogen population (NOTE: calculate the amount of organic C source based on its organic C content)
- Add 440 g of N per kg of coal (NOTE: calculate the amount of fertilizer based on its N content)
- Add 97 g P per kg of coal (NOTE: calculate the amount of fertilizer based on its P content)
- Add vitamins in the following amounts per kg coal
  - 0.333 g Biotin
  - 0.333 g Folic Acid
  - 1.667 g Pyrodoxine Hydrochloride
  - 0.833 g Thiamine Hydrochloride
  - 0.833 g Riboflavin
  - 0.833 g Nicotinic Acid
  - 0.833 g DL-Calcium Panthenate
  - 0.017 g Vitamin $B_{12}$
  - 0.833 g p-Aminobenzoic Acid
  - 0.833 g Lipoic Acid One example of an oil shale specific predetermined amendment may include:
- Add 17.5 to 70.0 g of N per kg of oil shale (NOTE: calculate the amount of fertilizer based on its N content)
- Add 4.0 to 15.5 g P per kg of oil shale (NOTE: calculate the amount of fertilizer based on its P content)
- Add vitamins in the following amounts per kg oil shale
  - 0.333 g Biotin
  - 0.333 g Folic Acid
  - 1.667 g Pyrodoxine Hydrochloride
  - 0.833 g Thiamine Hydrochloride
  - 0.833 g Riboflavin
  - 0.833 g Nicotinic Acid
  - 0.833 g DL-Calcium Panthenate
  - 0.017 g Vitamin $B_{12}$
  - 0.833 g p-Aminobenzoic Acid
  - 0.833 g Lipoic Acid Another example of an oil shale specific predetermined amendment may include:
- Add 50 to 200 g of organic C per kg oil shale to increase methanogen population (NOTE: calculate the amount of organic C source based on its organic C content)
- Add 35 to 140 g of N per kg of oil shale (NOTE: calculate the amount of fertilizer based on its N content)
- Add 7.75 to 31.00 g P per kg of oil shale (NOTE: calculate the amount of fertilizer based on its P content)
- Add vitamins in the following amounts per kg oil shale
  - 0.333 g Biotin
  - 0.333 g Folic Acid
  - 1.667 g Pyrodoxine Hydrochloride
  - 0.833 g Thiamine Hydrochloride
  - 0.833 g Riboflavin
  - 0.833 g Nicotinic Acid
  - 0.833 g DL-Calcium Panthenate
  - 0.017 g Vitamin $B_{12}$
  - 0.833 g p-Aminobenzoic Acid
  - 0.833 g Lipoic Acid One example of a lignite specific predetermined amendment may include:
- Add 170 g of N per kg of lignite (NOTE: calculate the amount of fertilizer based on its N content)
- Add 37 g P per kg of lignite (NOTE: calculate the amount of fertilizer based on its P content)
- Add vitamins in the following amounts per kg lignite
  - 0.333 g Biotin
  - 0.333 g Folic Acid
  - 1.667 g Pyrodoxine Hydrochloride
  - 0.833 g Thiamine Hydrochloride
  - 0.833 g Riboflavin
  - 0.833 g Nicotinic Acid
  - 0.833 g DL-Calcium Panthenate
  - 0.017 g Vitamin $B_{12}$
  - 0.833 g p-Aminobenzoic Acid
  - 0.833 g Lipoic Acid Another example of a lignite specific predetermined amendment may include:
- Add 478 g of organic C per kg lignite to increase methanogen population (NOTE: calculate the amount of organic C source based on its organic C content)
- Add 335 g of N per kg of lignite (NOTE: calculate the amount of fertilizer based on its N content)
- Add 75 g P per kg of lignite (NOTE: calculate the amount of fertilizer based on its P content)
- Add vitamins in the following amounts per kg lignite
  - 0.333 g Biotin
  - 0.333 g Folic Acid
  - 1.667 g Pyrodoxine Hydrochloride
  - 0.833 g Thiamine Hydrochloride
  - 0.833 g Riboflavin
  - 0.833 g Nicotinic Acid
  - 0.833 g DL-Calcium Panthenate
  - 0.017 g Vitamin $B_{12}$
  - 0.833 g p-Aminobenzoic Acid
  - 0.833 g Lipoic Acid Non-limiting examples of ex-situ applications which may be applicable to those hydrocarbon-bearing formations such as but not limited to coal, oil shale, lignite, peat, hydrocarbon-contaminated soil, petroleum sludge, waste coal, and the like may include:
1. A sample characterization of total organic carbon, total nitrogen, phosphorous, sulfide, sulfate, iron, methanogens, and the like.
2. Addition of alkali solutions and/or surfactants to increase availability of the materials to be treated.
3. Optimization of nutrients, add easy substrates for population growth, add compounds to eliminate inhibitors (e.g., sulfide).
4. Engineering temperature control to maintain 30-40° C. and anaerobic conditions of the ex-situ reactor (pit, aboveground structures).

Figure 17A:
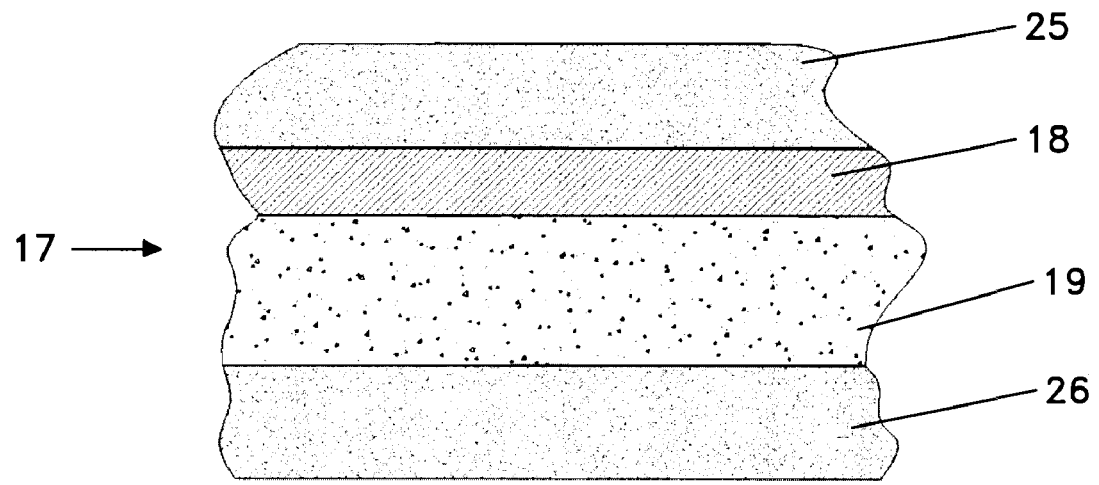
FIG. 17A-17F represents a hydrocarbon-bearing formation of which amendments may be carried to an oil shale layer to enhance biogenic methane production in accordance with some embodiments of the present invention.
Figure 17B:
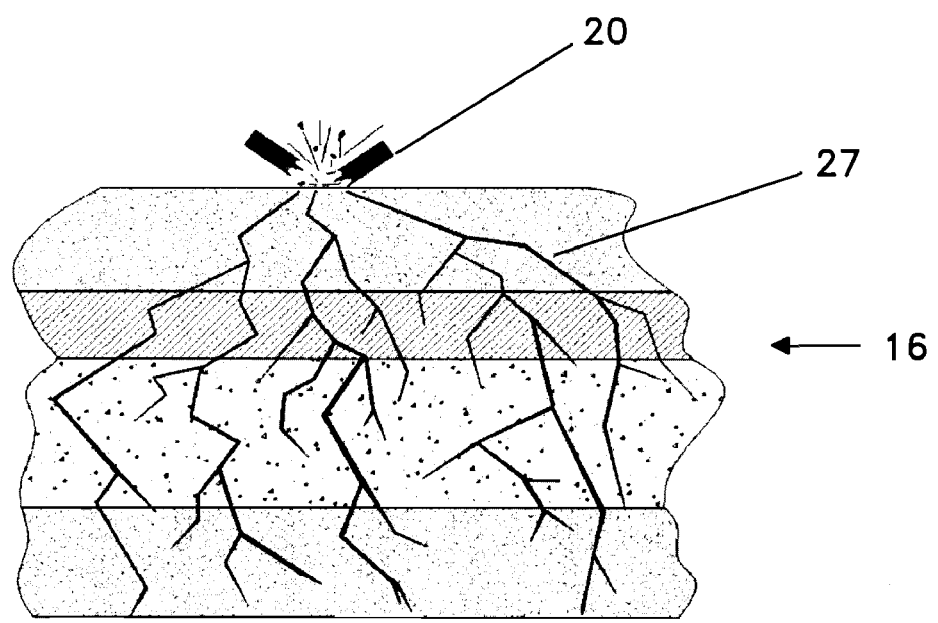

Embodiments of the present invention may include methods and systems for in-situ enhancement of biogenic methane production. This may be applied to various hydrocarbon-bearing formations. In particular, an embodiment may apply to oil shale formations (17) such as shown in FIGS. 17A-F. It may be desirable to locate an oil shale formation having perhaps an amendment-containing upper layer (18) and an oil shale layer (19). In embodiments, an oil shale formation may include an overburden (25), an amendment-containing upper layer (18), an oil shale layer (19), and perhaps even an underburden (26). In other embodiments, it may be desirable to locate an oil shale formation having perhaps at least one microbial population stimulation amendment. Depending on the oil shale source, some may not have upper layers or even overlying materials over an oil shale formation. In embodiment, microbial population stimulation amendment(s) may include an indigenous microbial population stimulation amendment of which they may be located throughout an oil shale formation. Fracturing of an oil shale formation or perhaps even of an amendment-containing upper layer of said oil shale formation may occur such as with an oil shale formation fracture element or perhaps even with an upper layer fracture element (20). Fractures (27) may occur throughout the oil shale formation as shown in FIG. 17B. A fracturing process may include drilling, breaking, an explosion, or the like of the upper layer as one skilled in the art could appreciate. A fractured oil shale layer or perhaps even a fractured upper layer may allow amendments that were originally present in a formation or perhaps in a layer to be loosen from or even broken apart. These amendments may then be delivered to at least one microbial population perhaps with a microbial population stimulation amendment delivery element. In other embodiments, amendments may then be carried from an upper layer to an oil shale layer perhaps with an upper layer amendment delivery element.

Figure 17C:
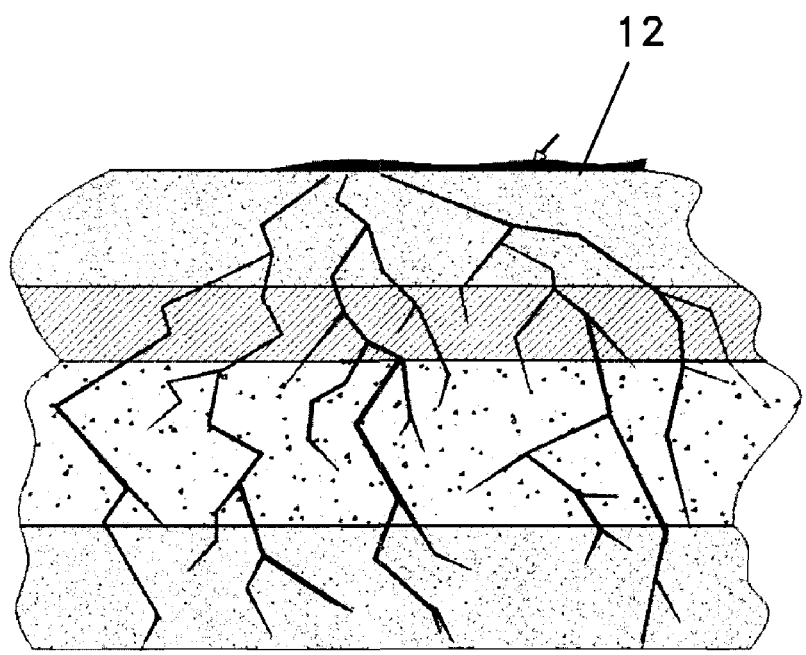
Figure 17D:
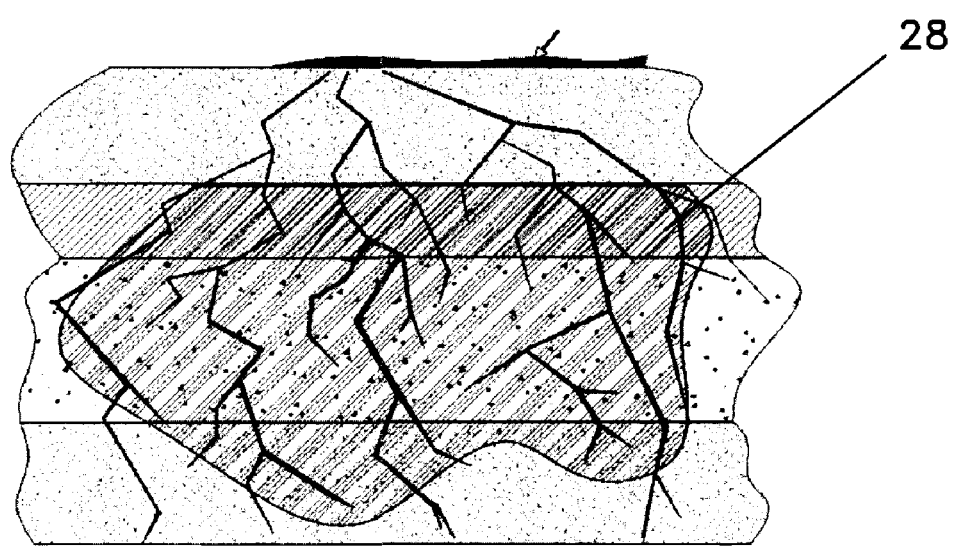
Figure 17E:
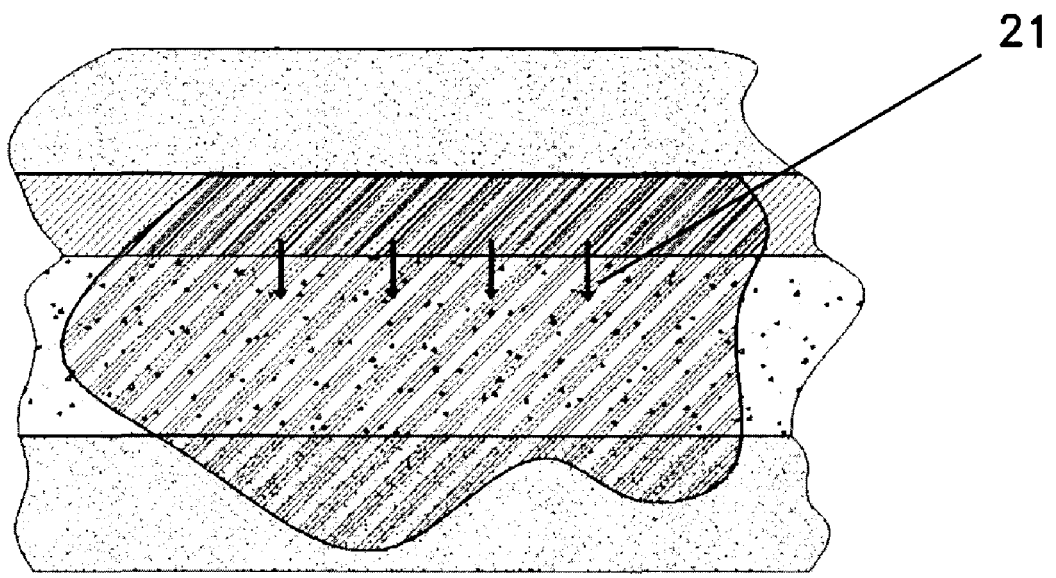
Figure 17F:
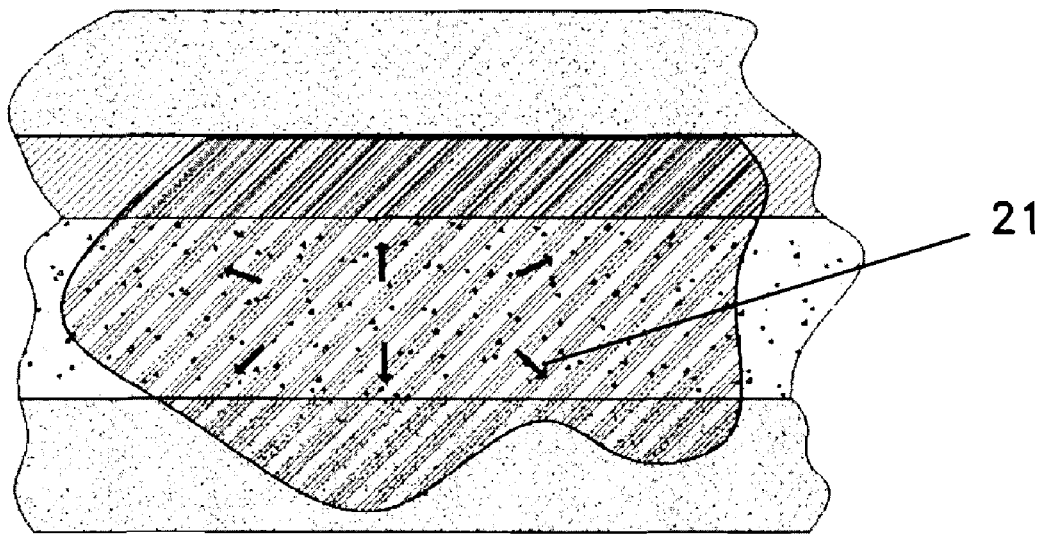

In embodiments, a microbial population stimulation amendment delivery element or perhaps even an upper layer amendment delivery element may include liquid which can be injected through the fractures of an oil shale formation, as shown in FIG. 17C. A liquid injection element can provide liquid (28) flowing throughout an oil shale formation and may even provide in other embodiment liquid flowing from an upper layer down to an oil shale layer as shown in FIG. 17D. Movement of at least one microbial population stimulation amendment (21) within a fractured oil shale formation can be understood in FIGS. 17E and 17F. Amendments (21) may spread throughout an oil shale layer. Embodiments may include a water injection element of which water may be injected through a fractured amendment-containing upper layer of an oil shale formation. In yet other embodiments, the present invention may provide a recycled water injection element of which recycled water may be injected through a fractured amendment-containing upper layer. Each of the various injection embodiments may carry amendments within an oil shale formation or perhaps even from an upper layer to an oil shale layer.

The newly delivered amendment(s) may perhaps stimulate at least one microbial population located in an oil shale formation. In embodiments, at least one microbial population may include an indigenous microbial population which may have pre-existed with an oil shale formation. At least one microbial population may even include at least one methanogen population, in embodiments. As described above, stimulation of microbial populations perhaps from microbial population stimulation amendment(s) may then generate methane. It may then be desirable to collect the produced methane perhaps even with a methane collection element as discussed herein.

A microbial population stimulation amendment may include but is not limited to amendments such as sodium bicarbonate, sodium carbonate, hydrated sodium carbonate, nahcolite containing amendments, trona containing amendments, any combination thereof, and the like. These amendments may provide appropriate stimulation of microbial populations in the oil shale layer to biogenically produce methane. This may provide a system to which methane production can be efficiently enhanced.

A vast majority of oil shale deposited in southwestern Wyoming, Green River, Wyo., northwestern Colorado and eastern Utah may have nahcolite interbedded with the oil shale. Fracturing of this material may be easily done due to the relatively soft nature of the rock as one skilled in the art can appreciate. Oil shales may tend to have low strength both in compression and in tension. The oil shale beds that underlie the trona beds may be small in volume compared to the massive oil shale beds noted above. Trona may be more difficult to fracture due to its inherent strength. It can test from 2500 to 7000 psi in compressive strength and could exhibit at least double the tensile strength of oil shale. Accordingly, trona could be fractured and dissolved in a similar manner as could be done with massive oil shale beds/deposits, or the like.

In yet other embodiments, it may be desirable to inject liquid and perhaps at least one additional amendment through a fractured amendment-containing upper layer of an oil shale formation such as with an additional amendment injection element. An additional amendment injection element may include the addition of amendments through an upper layer and delivery of the newly added amendment(s) to an oil shale layer. Additional amendments may include, but are not limited to, nitrogen, phosphorous, vitamins, organic carbon, biotin, folic acid, pyrodoxine hydrochloride, thiamine hydrochloride, riboflavin, nicotinic acid, DL-calcium panthenate, vitamin B12, p-aminobenzoic acid, liponic acid, any combination thereof, and the like. In other embodiments, additional amendments may include but are not limited to biowastes, lactate, milk, returned milk, nitrogen, phosphorous, vitamins, salts, micronutrients, surfactants, acids, bases, oxidants, acetic acid, sodium hydroxide, percarbonate, peroxide, sodium carbonate, sodium bicarbonate, hydrated sodium carbonate, any combination thereof, and the like.

As discussed herein, the present invention may include, in embodiments, an ex situ bioreactor to produce methane. Ex-situ systems may provide degradation and perhaps even enhancement of methane production from coal seam, waste coal, oil shale, coal, coal derivatives, peat, lignite, oil formations, tar sands, and the like. Ex-situ systems may be used after in-situ operations are completed in an attempt to extract all possible resources from a particular formation. Ex-situ systems may include in various embodiments: introduction of amendments such as substrates, nutrients, and the like; enhancement of organic matter released (physical, chemical, etc.); starvation and even selection of capable methanogens; diminishing sulfate competition; boosting a population of methanogens, any combination of these and the like as discussed herein. As an example, extracted CBM water can be used as a medium and stored in a sealed container, ditch, pit, underground containment or above ground system, or the like. An ex-situ system may include any type of non-subterranean environment. In an embodiment, fine coal and perhaps even low value coal may be crushed and may be amended with additional amendments (biowastes, lactate, returned milk, etc), and even with essential nutrients. Nitrite and ferrous iron can be added perhaps when a sulfate concentration may be high in the CBM water. A system can be set up so that methane produced may be collected and stored. After certain time of operation, a CBM water in the system may be injected into a site of interest to continue to generate CBM.

As an example, embodiments of the invention can be applied to a post-harvested site of altered oil shale, coal and the like. The invasive methods during the previous extraction activities such as oil shale retorting may create channels for a bioreaction as described above. A combination of enhancements may be applied to establish and enhance methane production from the residuals left in the site.

Operations such as oil shale retorting may leave residual hydrocarbon compounds in a post-harvested shale and water used during the operations. Water might be of environmental concern due to an elevated content of certain hydrocarbon compounds. The invention, in embodiments, can be applied to degrade hydrocarbon compounds in such water solely or perhaps even by mixing with other organic materials (e.g., agriculture wastes, oil shale structures and the like). The process may be carried out either in-situ or ex-situ. Biogenic methane may be produced as a side product during the biodegradation of the otherwise contaminant materials.

EXAMPLE 1

Figure 2:
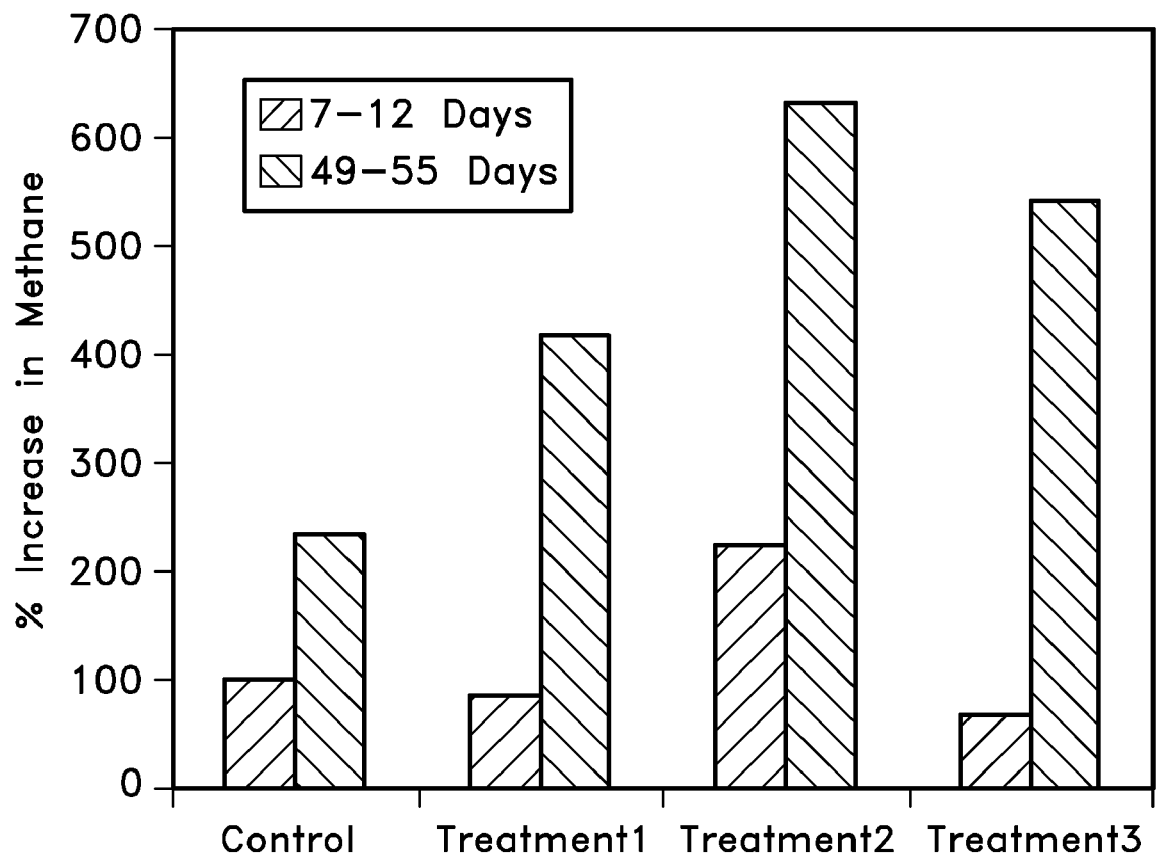
FIG. 2 shows an example of data from treatments on oil shale and the percentage of increase in methane in accordance with some embodiments of the present invention.

As an example, treatments were tested with oil shale in which results are shown in FIGS. 1 and 2. Treatment 1 includes nutrients. Treatment 2 includes milk and nutrients. Treatment 3 includes inoculated substances, milk and nutrients. In FIG. 1, the control was left at 100% at both 7-12 and 49-55 days and the percent increase was calculated relative to the control values. In FIG. 2, the control was set at 7-12 days at 100% and the percent increase was calculated relative to the control value at the first point.

EXAMPLE 2

Microbes were established in 160 mL glass serum bottles with septa to prevent oxygen exposure. Duplicates were established for each treatment, including non-amended sterile controls. Microbes were established so that 50 mL of headspace was remaining after setup for $CH_4$ production. Microbes were stored between 20-25° C. throughout the study. Amounts of substrate and water used for microbe establishment are shown in Table 2.

TABLE 2

Carbon source and water amounts used for microbe establishment.

| Carbon Source | Amount of Carbon Source, g | Water, mL |
| --- | --- | --- |
| Oil Shale | 75.0 | 63.0 |
| Coal | 64.3 | 54.0 |
| Lignite | 61.9 | 520 |
| Peat | 75.0 | 63.0 |
| Contaminated Soil | 77.4 | 65.0 |

Data from baseline characterizations were used to calculate nutrient amendments in corresponding microbes. Analytical results indicated that nitrogen (N) and phosphorus (P) were limiting for an optimal molar ratio of 100:30:3. Concentrations of N and P were increased using $NH_4Cl$ and $KH_2PO_4$ respectively. Other additions included dump milk and bacterial inhibitors (2-BESA sodium salt, vancomycin•HCl and $NaNO_2$). Tables 3-7 lists the treatments and amounts of treatments added to the microbes for each carbon source.

TABLE 3

Nutrients and inhibitors added to oil shale microbes.

| Microbe ID | CBM Water | Groundwater |
| --- | --- | --- |
| 1 | No additives | No additives |
| 2 | 0.0122 g 2-BESA sodium salt | 0.0122 g 2-BESA sodium salt |
| 3 | 0.0116 g Vancomycin•HCl | 0.0116 g Vancomycin•HCl |
| 4 | 0.0240 g $NaNO_2$ | 0.0240 g $NaNO_2$ |
| 5 | 1.9515 g $KH_2PO_4$<br>7.6688 g $NH_4Cl$ | 1.9494 g $KH_2PO_4$<br>7.6601 g $NH_4Cl$ |
| 6 | 12.6 mL Milk | 12.6 mL Milk |
| 7 | 12.6 mL Milk<br>7.9638 g $NH_4Cl$<br>2.0266 g $KH_2PO_4$ | 12.6 mL Milk<br>7.9551 g $NH_4Cl$<br>2.0245 g $KH_2PO_4$ |
| 8 | 12.6 mL Milk<br>7.9638 g $NH_4Cl$<br>2.0266 g $KH_2PO_4$<br>0.0116 g Vancomycin•HCl | 12.6 mL Milk<br>7.9551 g $NH_4Cl$<br>2.0245 g $KH_2PO_4$<br>0.0116 g Vancomycin•HCl |
| 9 | 12.6 mL Milk<br>7.9638 g $NH_4Cl$<br>2.0266 g $KH_2PO_4$<br>0.0122 g 2-BESA sodium salt | 12.6 mL Milk<br>7.9551 g $NH_4Cl$<br>2.0245 g $KH_2PO_4$<br>0.0122 g 2-BESA sodium salt |
| 10 | 12.6 mL Milk<br>7.9638 g $NH_4Cl$<br>2.0266 g $KH_2PO_4$<br>0.0240 g $NaNO_2$ | 12.6 mL Milk<br>7.9551 g $NH_4Cl$<br>2.0245 g $KH_2PO_4$<br>0.0240 g $NaNO_2$ |
| 11 | 1.9515 g $KH_2PO_4$<br>7.6688 g $NH_4Cl$<br>0.0240 g $NaNO_2$ | 1.9494 g $KH_2PO_4$<br>7.6601 g $NH_4Cl$<br>0.0240 g $NaNO_2$ |
| 12 | (Sterilized CBM Water)<br>(Sterilized Oil Shale) | (Sterilized Groundwater)<br>(Sterilized Oil Shale) |
| 13 | (Sterilized Oil Shale) | (Sterilized Oil Shale) |
| 14 | 12.6 mL Milk<br>7.9638 g $NH_4Cl$<br>2.0266 g $KH_2PO_4$<br>(Sterilized Oil Shale) | 12.6 mL Milk<br>7.9551 g $NH_4Cl$<br>2.0245 g $KH_2PO_4$<br>(Sterilized Oil Shale) |

TABLE 4

Nutrients and inhibitors added to coal microbes.

| Microbe ID | CBM WATER | WELL WATER |
| --- | --- | --- |
| 1 | Nothing | Nothing |
| 2 | 0.0122 g 2-BESA | 0.0122 g 2-BESA |
| 3 | 0.0116 g vancomycin | 0.0116 g vancomycin |
| 4 | 0.0240 g $NaNO_2$ | 0.0240 g $NaNO_2$ |
| 5 | 0.0125 g $NH_4Cl$<br>0.0043 g $KH_2PO_4$ | 0.0053 g $NH_4Cl$<br>0.0024 g $KH_2PO_4$ |
| 6 | 12.6 ml Milk | 12.6 ml Milk |
| 7 | 12.6 ml Milk<br>0.3075 g NH4Cl<br>0.0794 g KH2PO4 | 12.6 ml Milk<br>0.3003 g NH4Cl<br>0.0775 g KH2PO4 |
| 8 | 12.6 ml Milk<br>0.3075 g $NH_4Cl$<br>0.0794 g $KH_2PO_4$<br>0.0116 g vancomycin | 12.6 ml Milk<br>0.3003 g $NH_4Cl$<br>0.0775 g $KH_2PO_4$<br>0.0116 g vancomycin |
| 9 | 12.6 ml Milk<br>0.3075 g $NH_4Cl$<br>0.0794 g $KH_2PO_4$<br>0.0122 g 2-BESA | 12.6 ml Milk<br>0.3003 g $NH_4Cl$<br>0.0775 g $KH_2PO_4$<br>0.0122 g 2-BESA |
| 10 | 12.6 ml Milk<br>0.3075 g $NH_4Cl$<br>0.0794 g $KH_2PO_4$<br>0.0240 g $NaNO_2$ | 12.6 ml Milk<br>0.3003 g $NH_4Cl$<br>0.0775 g $KH_2PO_4$<br>0.0240 g $NaNO_2$ |
| 11 | 0.0125 g $NH_4Cl$<br>0.0043 g $KH_2PO_4$<br>0.0240 g $NaNO_2$ | 0.0053 g $NH_4Cl$<br>0.0024 g $KH_2PO_4$<br>0.0240 g $NaNO_2$ |
| 12 | Sterile Solid<br>Sterile Water | Sterile Solid<br>Sterile Water |
| 13 | Sterile Solid<br>Live Water | Sterile Solid<br>Live Water |
| 14 | 12.6 ml Milk<br>0.3075 g $NH_4Cl$<br>0.0794 g $KH_2PO_4$<br>Sterile Solid<br>Live Water | 12.6 ml Milk<br>0.3003 g $NH_4Cl$<br>0.0775 g $KH_2PO_4$<br>Sterile Solid<br>Live Water |

TABLE 5

Nutrients and inhibitors added to lignite microbes.

| Microbe ID | CBM WATER | WELL WATER |
|---|---|---|
| 1 | Nothing | Nothing |
| 2 | 0.0122 g 2-BESA | 0.0122 g 2-BESA |
| 3 | 0.0116 g vancomycin | 0.0116 g vancomycin |
| 4 | 0.0240 g $NaNO_2$ | 0.0240 g $NaNO_2$ |
| 5 | 0.0251 g $NH_4Cl$<br>0.0043 g $KH_2PO_4$ | 0.0182 g $NH_4Cl$<br>0.0038 g $KH_2PO_4$ |
| 6 | 12.6 ml Milk | 12.6 ml Milk |
| 7 | 12.6 ml Milk<br>0.3201 g NH4Cl<br>0.0794 g KH2PO4 | 12.6 ml Milk<br>0.3132 g NH4Cl<br>0.0789 g KH2PO4 |
| 8 | 12.6 ml Milk<br>0.3201 g $NH_4Cl$<br>0.0794 g $KH_2PO_4$<br>0.0116 g vancomycin | 12.6 ml Milk<br>0.3132 g $NH_4Cl$<br>0.0789 g $KH_2PO_4$<br>0.0116 g vancomycin |
| 9 | 12.6 ml Milk<br>0.3201 g $NH_4Cl$<br>0.0794 g $KH_2PO_4$<br>0.0122 g 2-BESA | 12.6 ml Milk<br>0.3132 g $NH_4Cl$<br>0.0789 g $KH_2PO_4$<br>0.0122 g 2-BESA |
| 10 | 12.6 ml Milk<br>0.3201 g $NH_4Cl$<br>0.0794 g $KH_2PO_4$<br>0.0240 g $NaNO_2$ | 12.6 ml Milk<br>0.3132 g $NH_4Cl$<br>0.0789 g $KH_2PO_4$<br>0.0240 g $NaNO_2$ |
| 11 | 0.0251 g $NH_4Cl$<br>0.0043 g $KH_2PO_4$<br>0.0240 g $NaNO_2$ | 0.0182 g $NH_4Cl$<br>0.0038 g $KH_2PO_4$<br>0.0240 g $NaNO_2$ |
| 12 | Sterile Solid<br>Sterile Water | Sterile Solid<br>Sterile Water |
| 13 | Sterile Solid<br>Live Water | Sterile Solid<br>Live Water |
| 14 | 12.6 ml Milk<br>0.3201 g $NH_4Cl$<br>0.0794 g $KH_2PO_4$<br>Sterile Solid<br>Live Water | 12.6 ml Milk<br>0.3132 g $NH_4Cl$<br>0.0789 g $KH_2PO_4$<br>Sterile Solid<br>Live Water |

TABLE 6

Nutrients and inhibitors added to peat microbes.

| Microbe ID | CBM WATER | WELL WATER |
|---|---|---|
| 1 | Nothing | Nothing |
| 2 | 0.0122 g 2-BESA | 0.0122 g 2-BESA |
| 3 | 0.0116 g vancomycin | 0.0116 g vancomycin |
| 4 | 0.0240 g $NaNO_2$ | 0.0240 g $NaNO_2$ |
| 5 | 0.0685 g $NH_4Cl$<br>0.0183 g $KH_2PO_4$ | 0.0601 g $NH_4Cl$<br>0.0161 g $KH_2PO_4$ |
| 6 | 12.6 ml Milk | 12.6 ml Milk |
| 7 | 12.6 ml Milk<br>3.61 g NH4Cl<br>0.9191 g KH2PO4 | 12.6 ml Milk<br>3.60 g NH4Cl<br>0.9169 g KH2PO4 |
| 8 | 12.6 ml Milk<br>3.61 g NH4Cl<br>0.9191 g $KH_2PO_4$<br>0.0116 g vancomycin | 12.6 ml Milk<br>3.60 g NH4Cl<br>0.9169 g $KH_2PO_4$<br>0.0116 g vancomycin |
| 9 | 12.6 ml Milk<br>3.61 g NH4Cl<br>0.9191 g $KH_2PO_4$<br>0.0122 g 2-BESA | 12.6 ml Milk<br>3.60 g NH4Cl<br>0.9169 g $KH_2PO_4$<br>0.0122 g 2-BESA |
| 10 | 12.6 ml Milk<br>3.61 g NH4Cl<br>0.9191 g $KH_2PO_4$<br>0.0240 g $NaNO_2$ | 12.6 ml Milk<br>3.60 g NH4Cl<br>0.9169 g $KH_2PO_4$<br>0.0240 g $NaNO_2$ |
| 11 | 0.0685 g $NH_4Cl$<br>0.0183 g $KH_2PO_4$<br>0.0240 g $NaNO_2$ | 0.0601 g $NH_4Cl$<br>0.0161 g $KH_2PO_4$<br>0.0240 g $NaNO_2$ |
| 12 | Sterile Solid<br>Sterile Water | Sterile Solid<br>Sterile Water |
| 13 | Sterile Solid<br>Live Water | Sterile Solid<br>Live Water |
| 14 | 12.6 ml Milk<br>3.61 g NH4Cl<br>0.9191 g $KH_2PO_4$<br>Sterile Solid<br>Live Water | 12.6 ml Milk<br>3.60 g NH4Cl<br>0.9169 g $KH_2PO_4$<br>Sterile Solid<br>Live Water |

TABLE 7

Nutrients and inhibitors added to contaminated soil microbes.

| Microbe ID | CBM WATER | WELL WATER |
|---|---|---|
| 1 | Nothing | Nothing |
| 2 | 0.0122 g 2-BESA | 0.0122 g 2-BESA |
| 3 | 0.0116 g vancomycin | 0.0116 g vancomycin |
| 4 | 0.0240 g $NaNO_2$ | 0.0240 g $NaNO_2$ |
| 5 | 12.92 g $NH_4Cl$<br>3.29 g $KH_2PO_4$ | 12.92 g $NH_4Cl$<br>3.29 g $KH_2PO_4$ |
| 6 | 13 ml Milk | 13 ml Milk |
| 7 | 13 ml Milk<br>16.58 g NH4Cl<br>4.22 g KH2PO4 | 13 ml Milk<br>16.57 g NH4Cl<br>4.22 g KH2PO4 |
| 8 | 13 ml Milk<br>16.58 g NH4Cl<br>4.22 g $KH_2PO_4$<br>0.0116 g vancomycin | 13 ml Milk<br>16.57 g NH4Cl<br>4.22 g $KH_2PO_4$<br>0.0116 g vancomycin |
| 9 | 13 ml Milk<br>16.58 g NH4Cl<br>4.22 g $KH_2PO_4$<br>0.0122 g 2-BESA | 13 ml Milk<br>16.57 g NH4Cl<br>4.22 g $KH_2PO_4$<br>0.0122 g 2-BESA |
| 10 | 13 ml Milk<br>16.58 g NH4Cl<br>4.22 g $KH_2PO_4$<br>0.0240 g $NaNO_2$ | 13 ml Milk<br>16.57 g NH4Cl<br>4.22 g $KH_2PO_4$<br>0.0240 g $NaNO_2$ |
| 11 | 12.92 g $NH_4Cl$<br>3.29 g $KH_2PO_4$<br>0.0240 g $NaNO_2$ | 12.92 g $NH_4Cl$<br>3.29 g $KH_2PO_4$<br>0.0240 g $NaNO_2$ |
| 12 | Sterile Solid<br>Sterile Water | Sterile Solid<br>Sterile Water |
| 13 | Sterile Solid<br>Live Water | Sterile Solid<br>Live Water |
| 14 | 13 ml Milk<br>16.58 g NH4Cl<br>4.22 g $KH_2PO_4$<br>Sterile Solid<br>Live Water | 13 ml Milk<br>16.57 g NH4Cl<br>4.22 g $KH_2PO_4$<br>Sterile Solid<br>Live Water |

EXAMPLE 3

A separate set of microbes were established to increase the bioavailability of organics. This was done by pre-treating the crushed oil shale with 1 M sodium hydroxide (NaOH). 1 M NaOH solution was added to the oil shale until a pH of 13 was attained and the mixture was allowed to react for 24 hours at room temperature and under nitrogen atmosphere. The pH was lowered to 9.8 by adding HCl before the addition of treatments and increasing the liquid volume to 63 mL. As before, the microbes were created anaerobically in the same manner as outlined before. The information Table 8 lists the microbes created along with corresponding amendments.

TABLE 8

Nutrients and inhibitors added to groundwater (63 mL) mixed with pre-treated oil shale (75 g) with NaOH.

| Microbe ID | Groundwater |
|---|---|
| 1 | No Additives |
| 2 | 1.9494 g $KH_2PO_4$<br>7.6601 g $NH_4Cl$ |

TABLE 8-continued

Nutrients and inhibitors added to groundwater (63 mL) mixed with pre-treated oil shale (75 g) with NaOH.

| Microbe ID | Groundwater |
|---|---|
| 3 | 12.6 ml milk |
| 4 | 2.0245 g $KH_2PO_4$ <br> 7.9551 g $NH_4Cl$ <br> 12.6 ml milk |
| 5 | (Sterilized Groundwater) <br> (Sterilized Oil Shale) |
| 6 | (Sterilized Oil Shale) <br> No Amendments |
| 7 | (Sterilized Oil Shale) <br> 2.045 g $KH_2PO_4$ <br> 7.9551 g $NH_4Cl$ <br> 12.6 ml milk |

Figure 3:
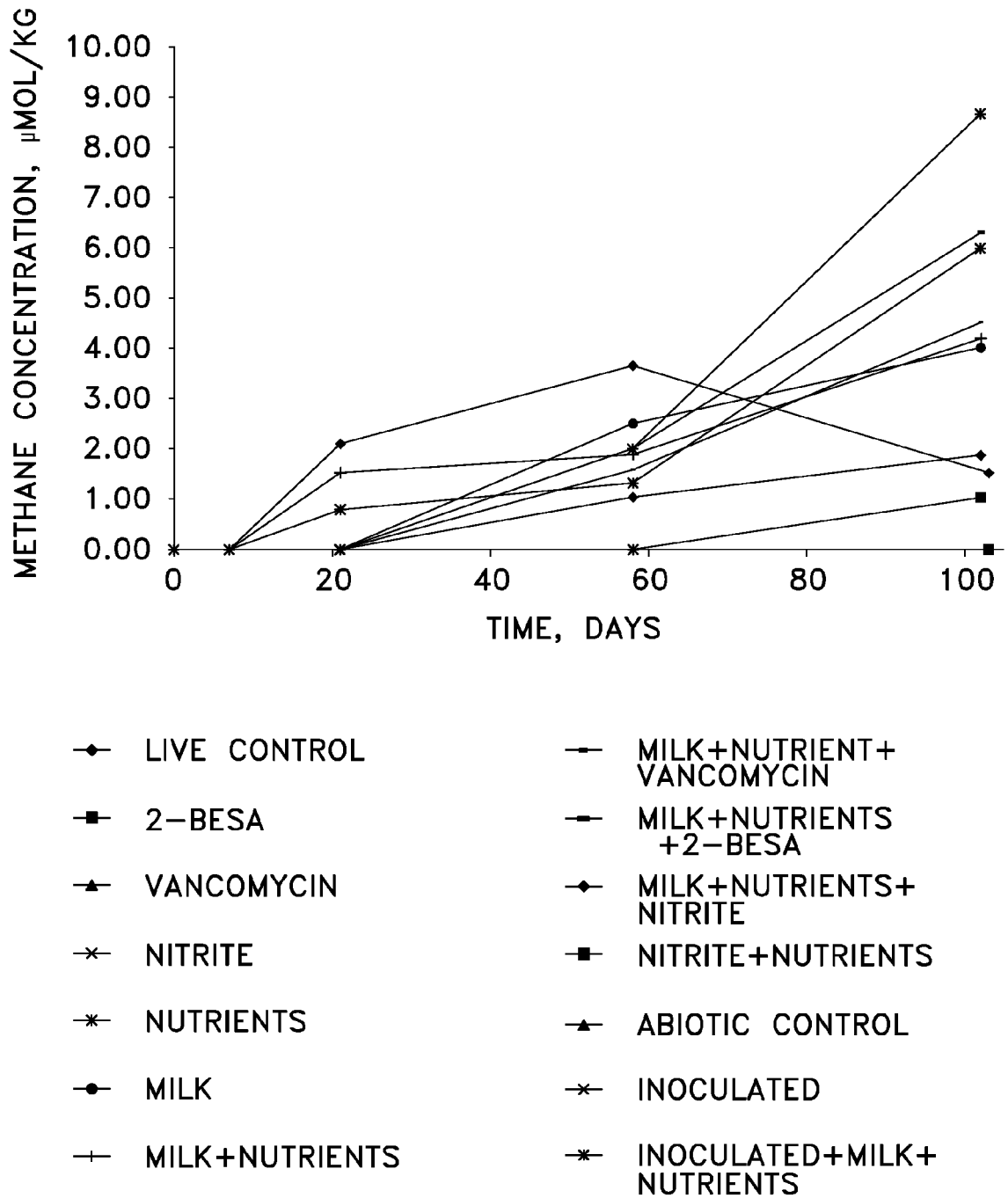
FIG. 3 shows an example of data for cumulative methane production from microbes with coal and CBM co-produced water in accordance with some embodiments of the present invention.
Figure 4:
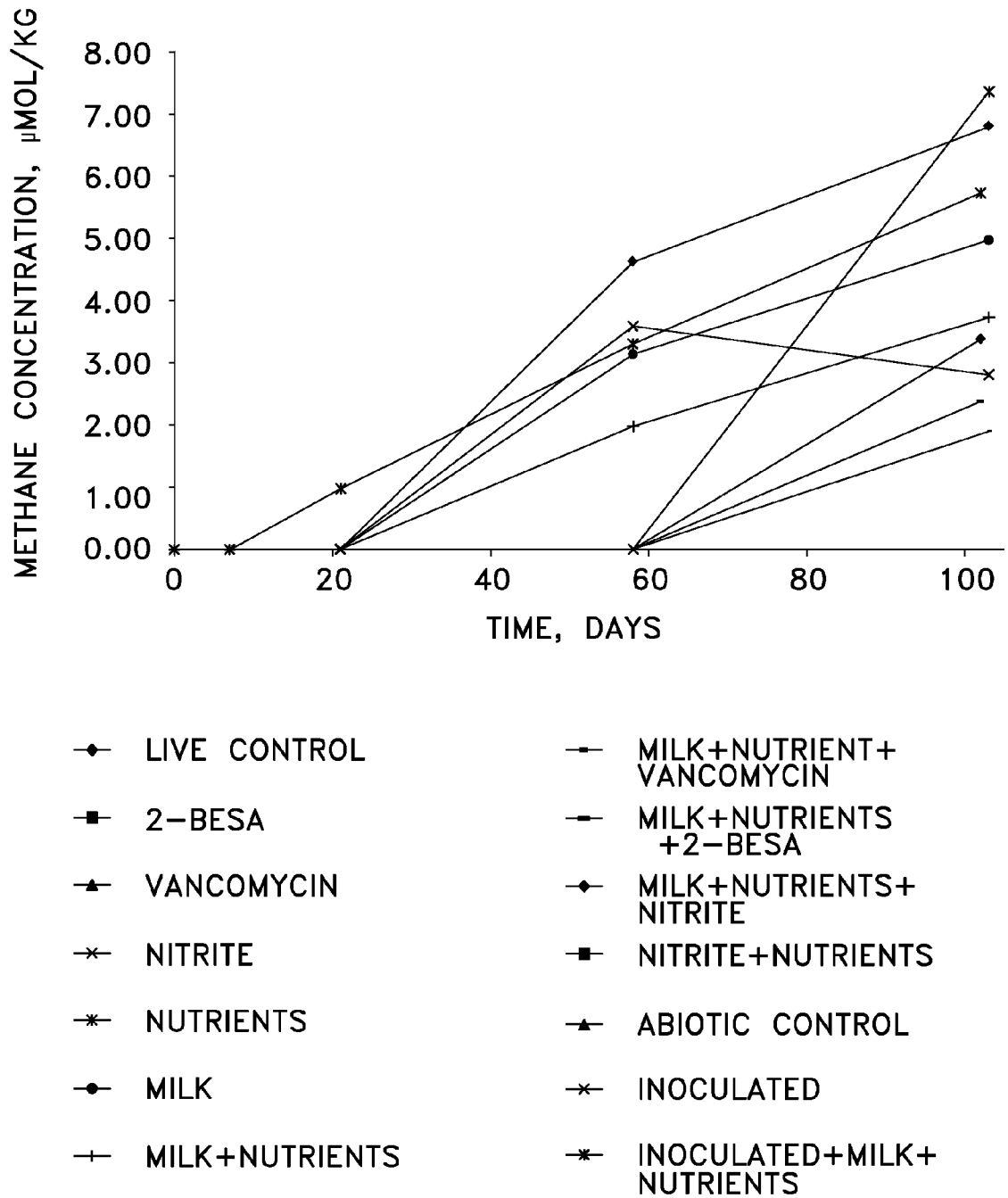
FIG. 4 shows an example of data for cumulative methane production from microbes with coal and groundwater in accordance with some embodiments of the present invention.
Figure 5:
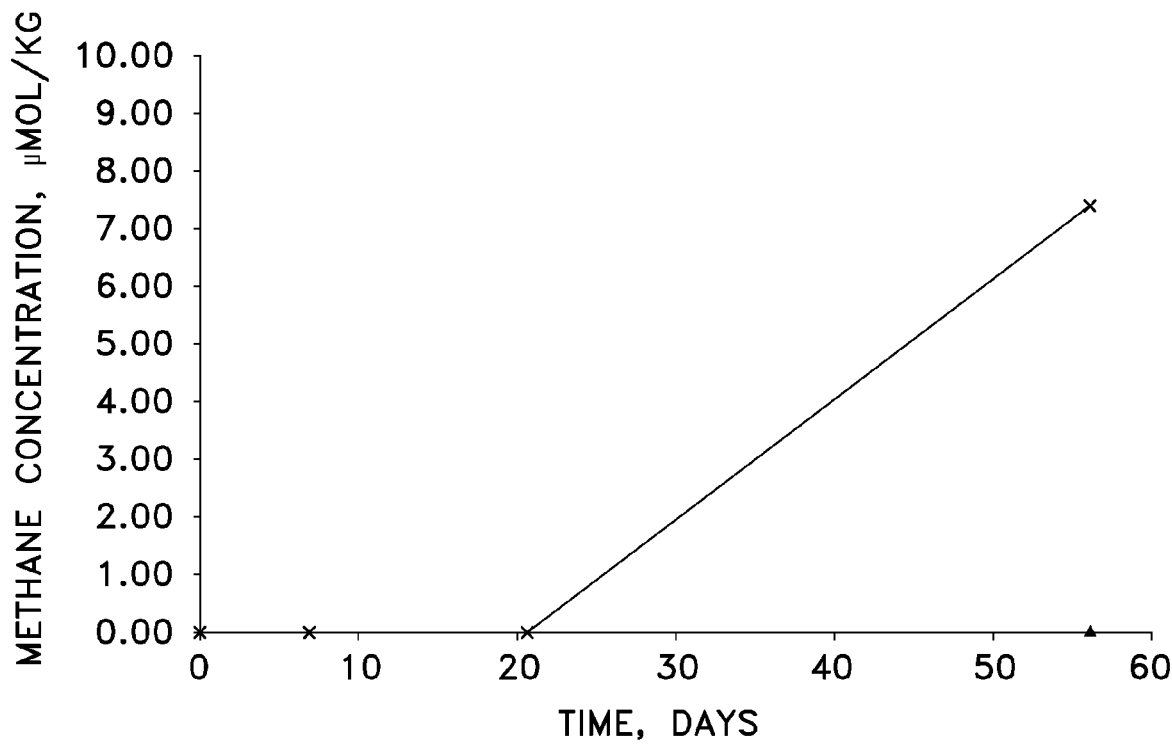
FIG. 5 shows an example of data for cumulative methane production from microbes with lignite and CBM co-produced water in accordance with some embodiments of the present invention.
Figure 6:
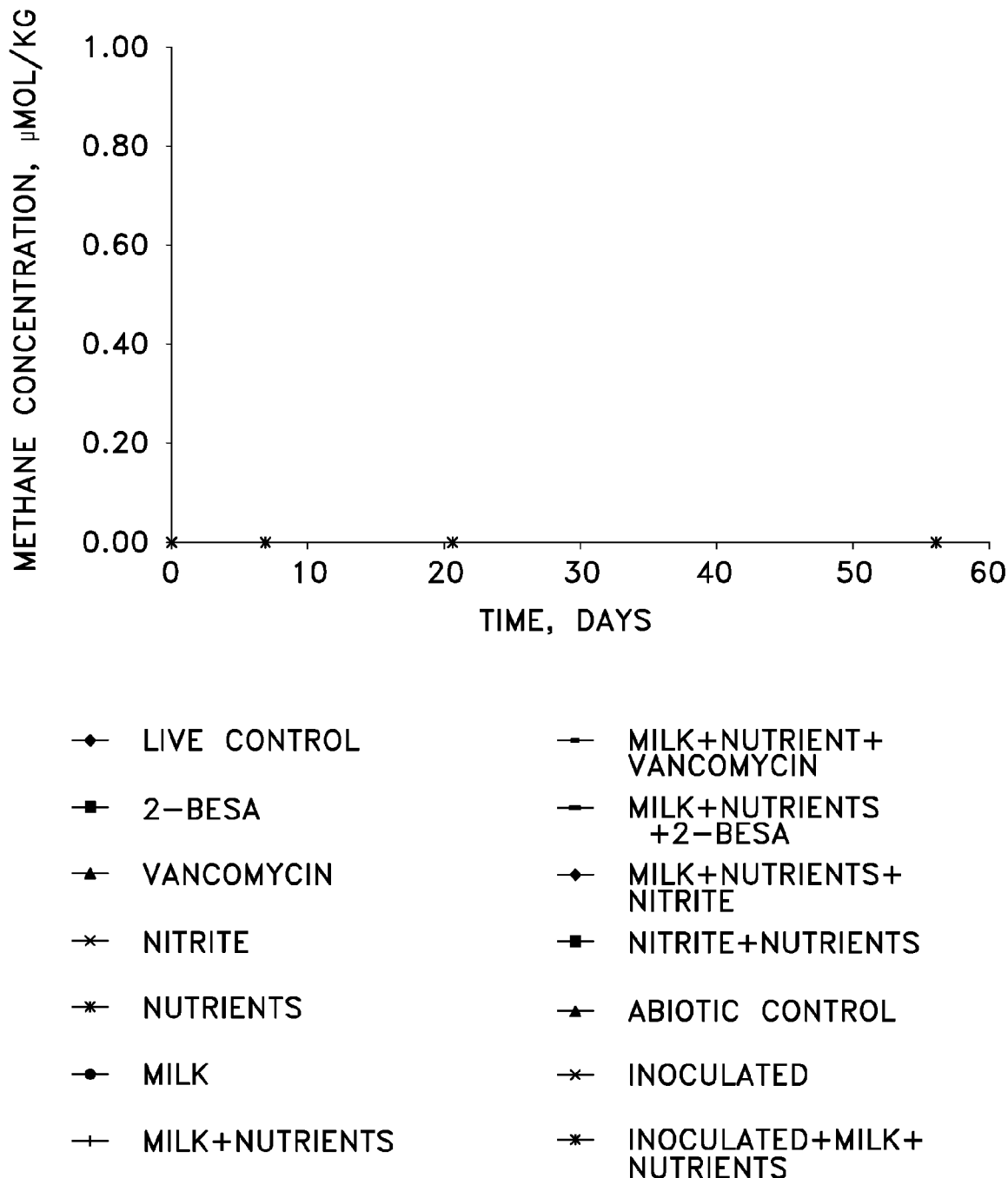
FIG. 6 shows an example of data for cumulative methane production from microbes with lignite and groundwater in accordance with some embodiments of the present invention.
Figure 7:
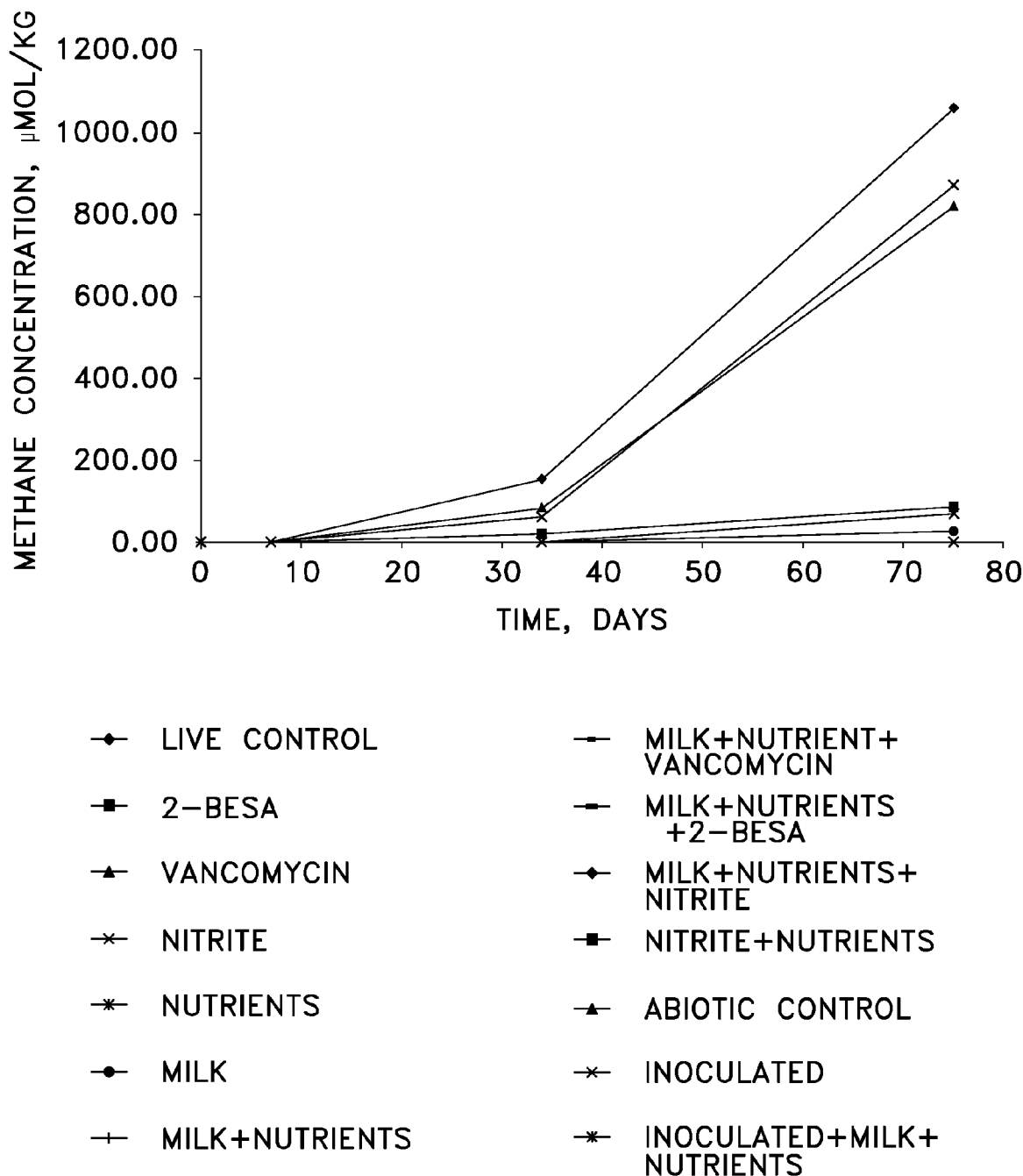
FIG. 7 shows an example of data for cumulative methane production from microbes with diesel-contaminated soil and CBM co-produced water in accordance with some embodiments of the present invention.
Figure 8:
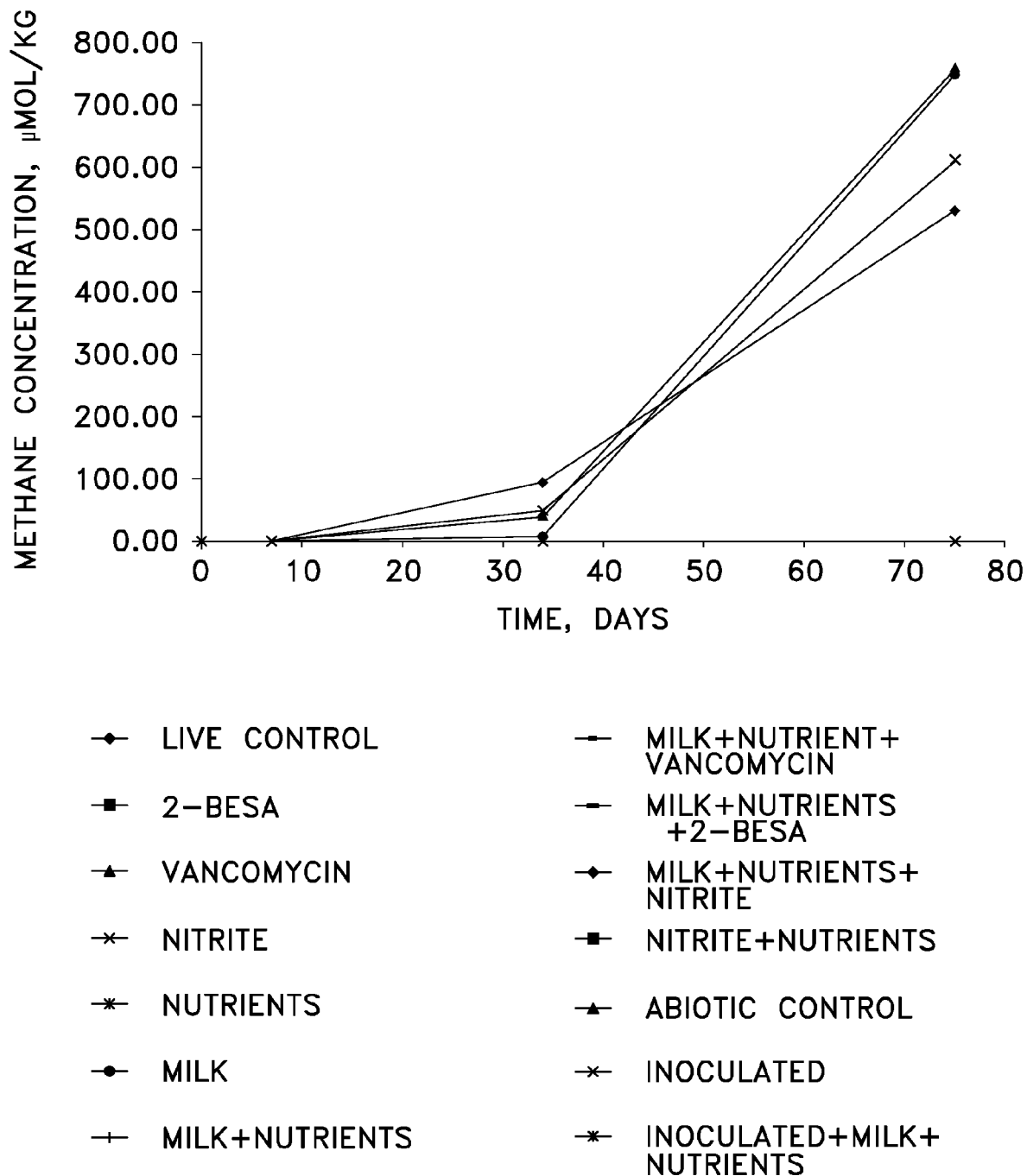
FIG. 8 shows an example of data for cumulative methane production from microbes with diesel-contaminated soil and groundwater in accordance with some embodiments of the present invention.
Figure 9:
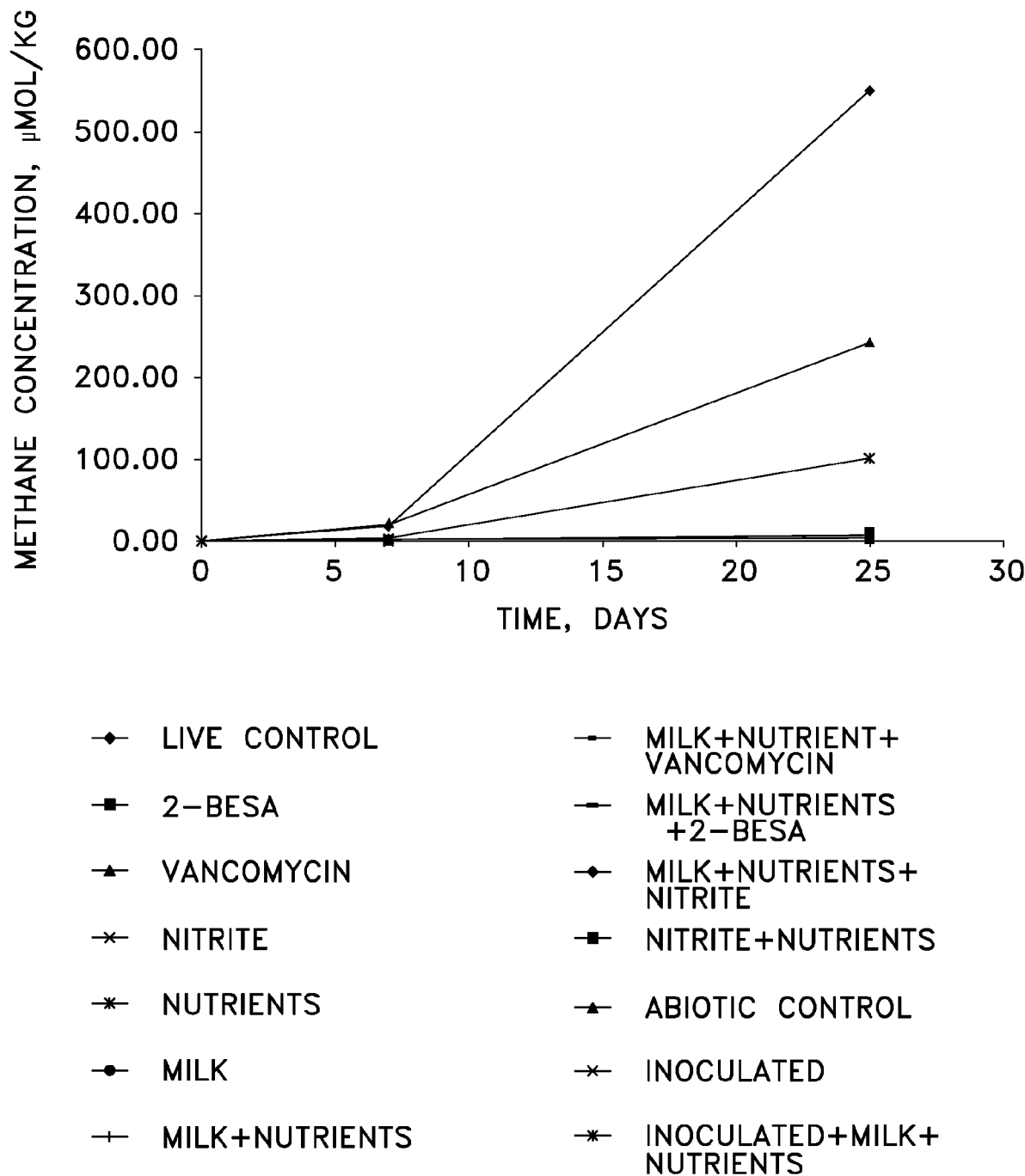
FIG. 9 shows an example of data for cumulative methane production from microbes with peat and CBM co-produced water in accordance with some embodiments of the present invention.
Figure 10:
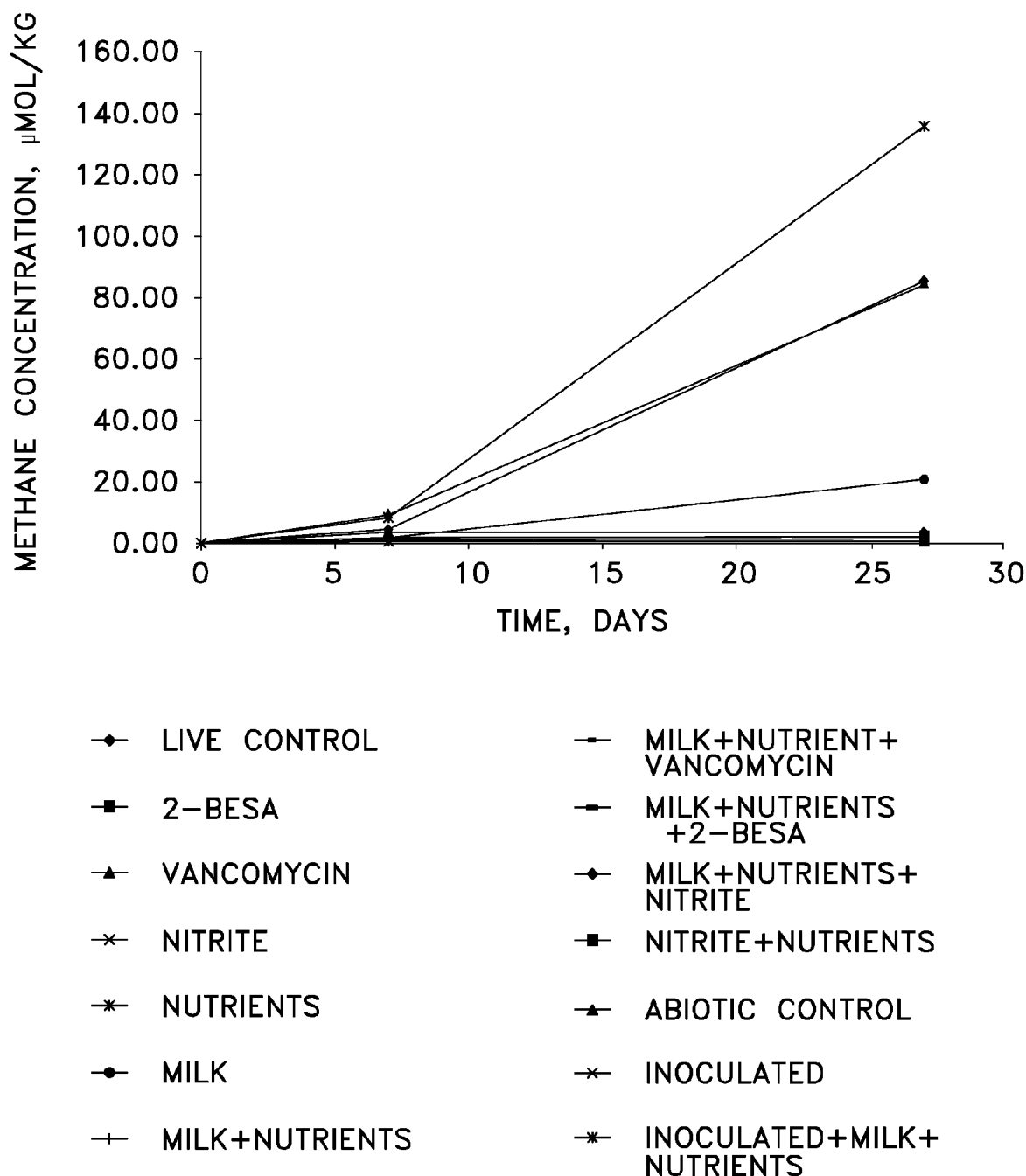
FIG. 10 shows an example of data for cumulative methane production from microbes with peat and groundwater in accordance with some embodiments of the present invention.

The results may show that nutrient-amended, especially nutrient plus substrate amended, treatments produced the highest amount of methane from microbes containing coal CBM co-produced water, as shown in FIG. 3. Nutrients may substantially increase the rate of methane production after 60 days from microbes containing coal and groundwater, as shown in FIG. 4. The cumulative amount of methane produced from those treatments surpassed the live control after 100 days. Nutrient amendments may have had little effect on methane production in microbes containing lignite, as shown in FIGS. 5 and 6. The addition of nutrients to the diesel-contaminated soil may have had an inhibitory effect since the methane production in the controls was occurring at a greater rate, as shown in FIGS. 7 and 8. Aerobic bacteria may be dominant in numbers in the soil, which could consume the remaining oxygen in the system and produce carbon dioxide from the oxidation of the hydrocarbons. Other populations of anaerobic bacteria, such as facultative and strictly denitrifying bacteria, may exist in higher numbers in the soil, which may breakdown hydrocarbons to simpler molecules and carbon dioxide; however, methanogen population were not detected in this soil. Therefore, only the groundwater and CBM co-produced water may have supplied a methanogen population. An incubation period of greater than 60 days may be necessary for methanogenic conditions to dominate. FIG. 9 shows the cumulative methane production from microbes with peat and CBM co-produced water. Nutrient additions to microbes containing peat did have a positive effect on methane production as shown in FIG. 10.

Figure 11:
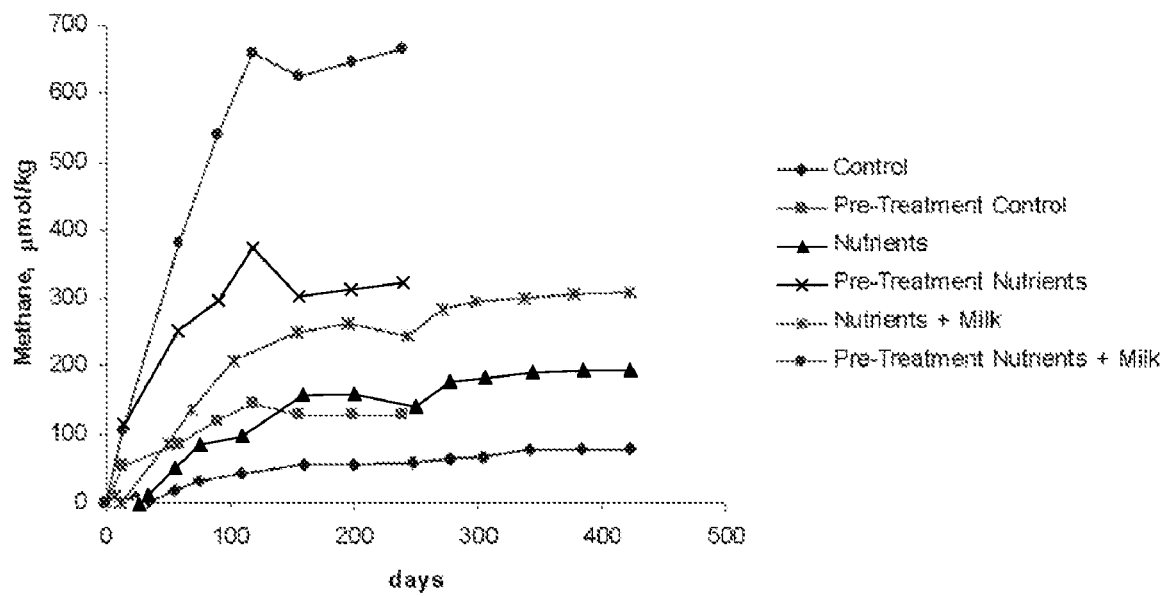
FIG. 11 shows an example of data for cumulative methane production from microbes with oil shale and groundwater in accordance with some embodiments of the present invention.
Figure 12A:
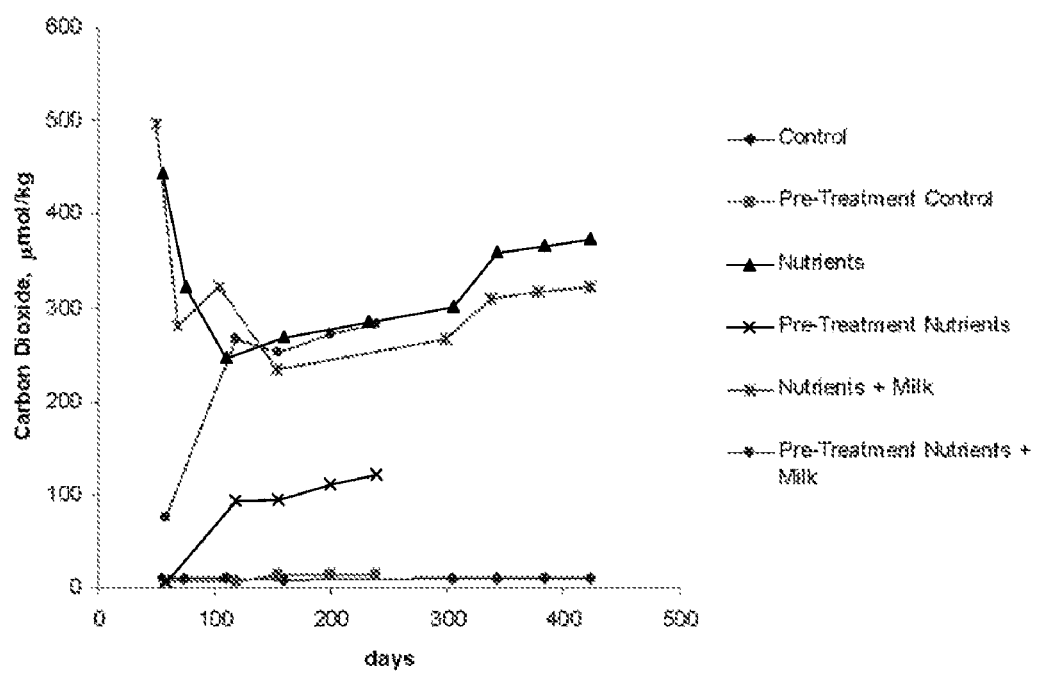
FIG. 12A shows an example of data for cumulative carbon dioxide production from gas produced in microbes with oil shale and groundwater in accordance with some embodiments of the present invention.
Figure 12B:
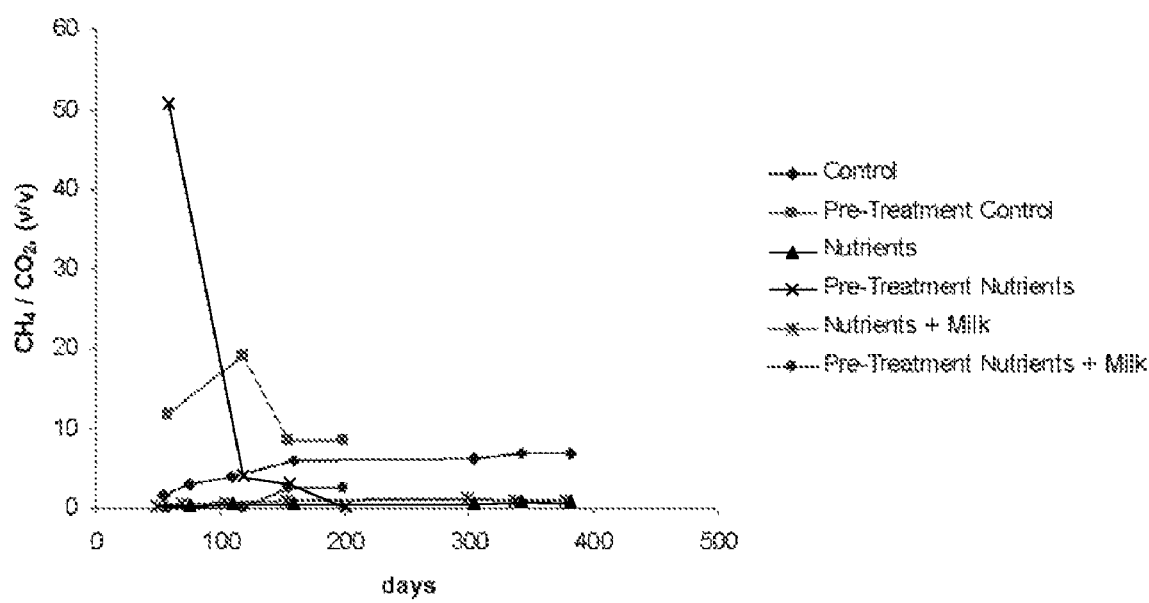
FIG. 12B shows an example of data for methane to carbon dioxide ratios from gas produced in microbes with oil shale and groundwater in accordance with some embodiments of the present invention.

The results from the groundwater-oil shale microbes may show that while methane production rate stabilizes, a higher concentration of carbon dioxide may be produced, as shown in FIGS. 11, 12a and 12b. This result may also be occurring with the groundwater-oil shale microbes containing the pre-treated oil shale. One possible problem was that the temperature of the room (~20° C.) was not optimal for methanogenesis, and a temperature of ~30° C. could be more adequate since this is the estimated temperature of oil shale at its source depth. The microbes were split into two groups: incubated at 30° C. and incubated at room temperature.

Figure 13A:
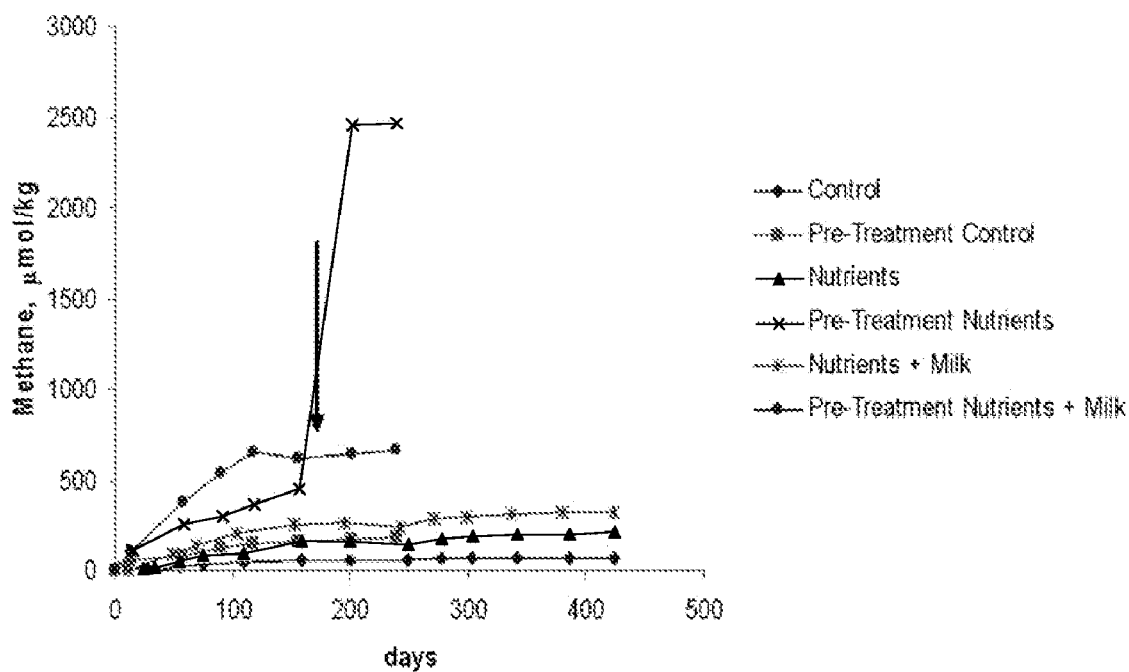
FIGS. 13A and 13B show an example of data for cumulative methane production from microbes with oil shale and groundwater which were incubated at 30° C. after 180 days in accordance with some embodiments of the present invention.
Figure 13B:
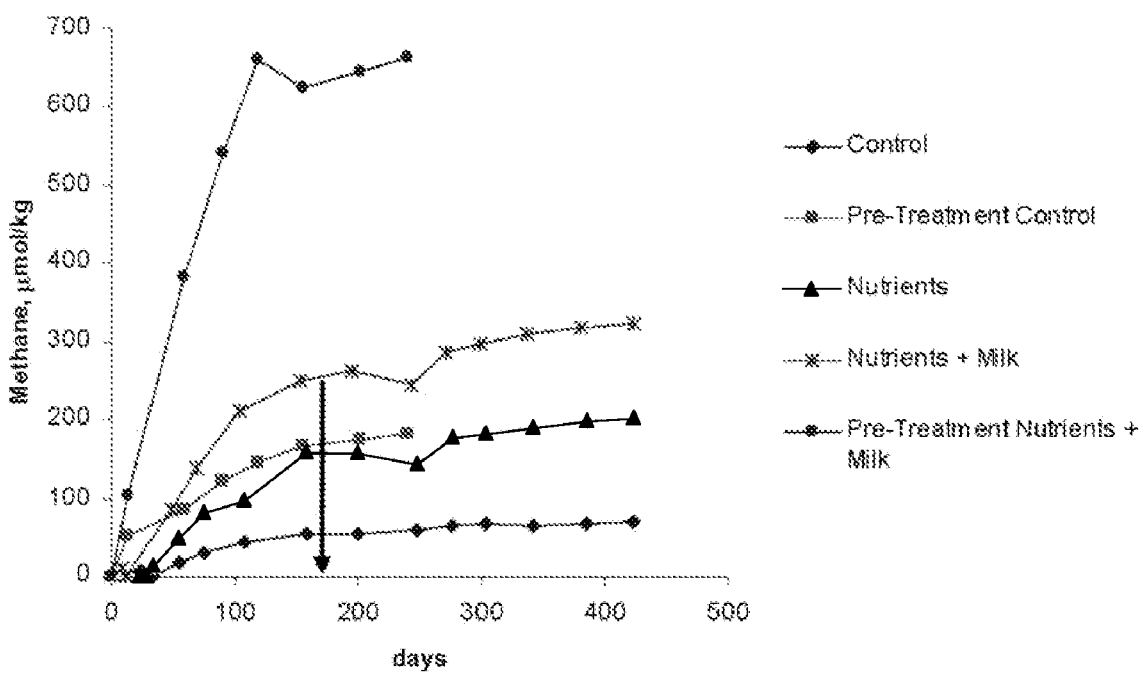
Figure 14A:
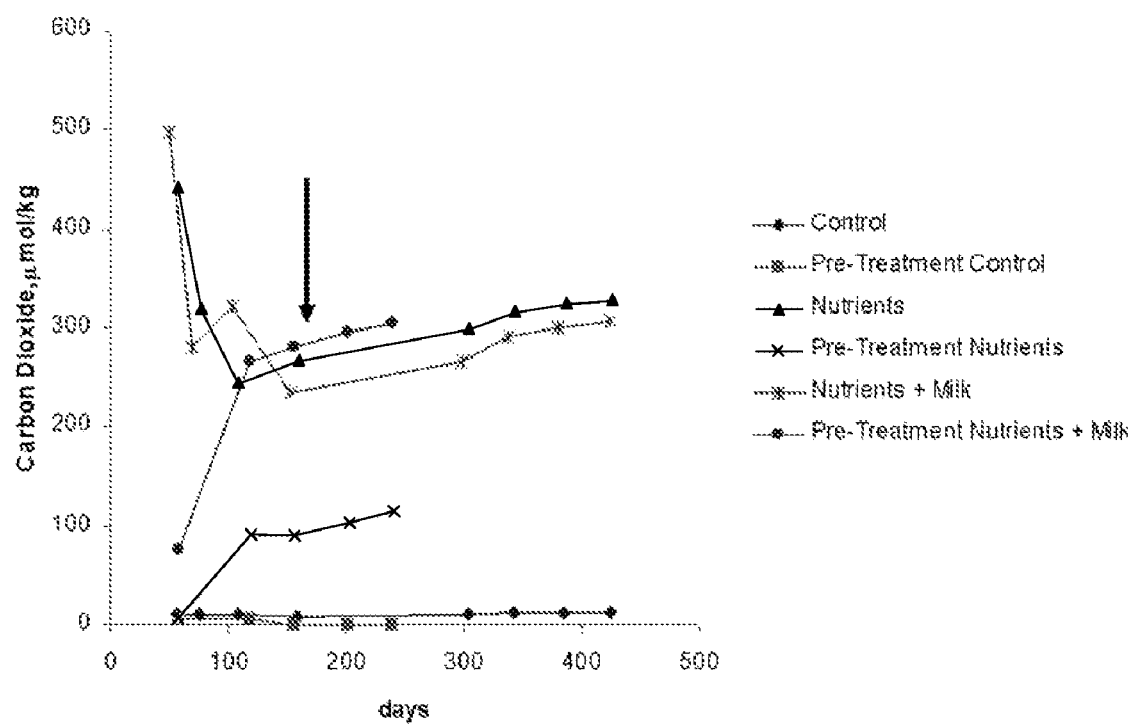
FIG. 14A shows an example of data for cumulative carbon dioxide production from gas produced in microbes with oil shale and groundwater which were incubated at 30° C. after 180 days in accordance with some embodiments of the present invention.
Figure 14B:
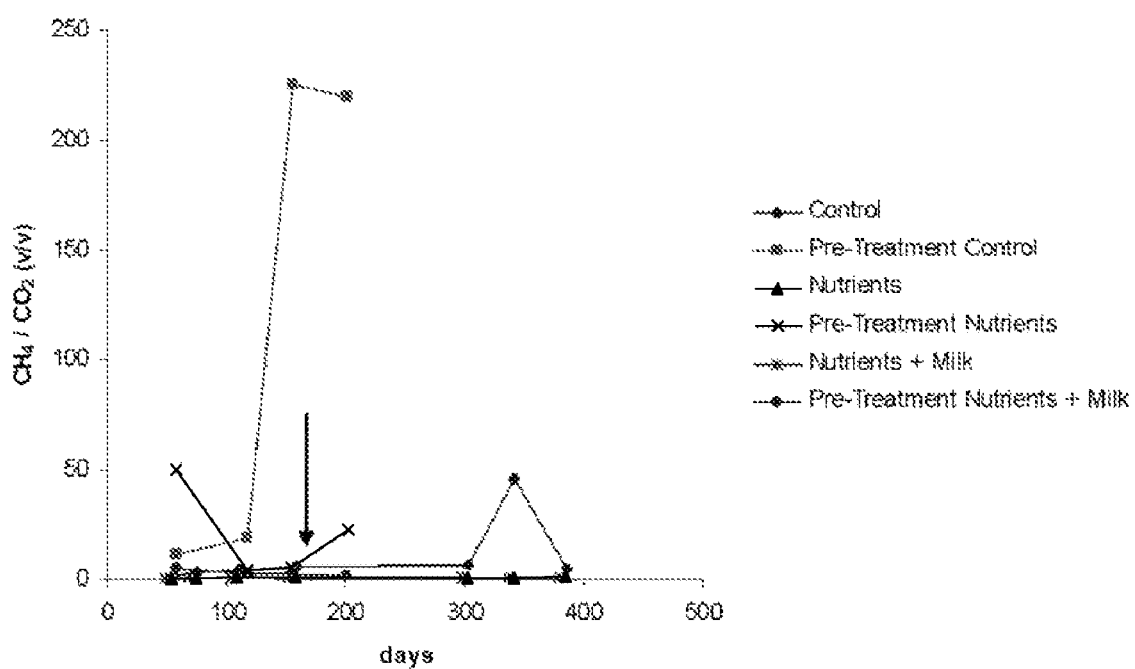
FIG. 14B shows an example of data for methane to carbon dioxide ratios from gas produced in microbes with oil shale and groundwater which were incubated at 30° C. after 180 days in accordance with some embodiments of the present invention.

In general, incubation at 30° C. may increase methane production rate and may increase the rate of carbon dioxide, see FIGS. 13a, 13b and 14a. Pre-treatment with nutrients may have a 30 fold increase in methane production rate, while the rate of carbon dioxide may decrease. This may substantially increase the methane to carbon dioxide volume ratio to more than 22, see FIG. 14b. This may suggest that pre-treatment and enhancement injections into oil shale reservoirs can substantially increase the rate of methane production and may reduce an amount of carbon dioxide.

EXAMPLE 4

Figure 15A:
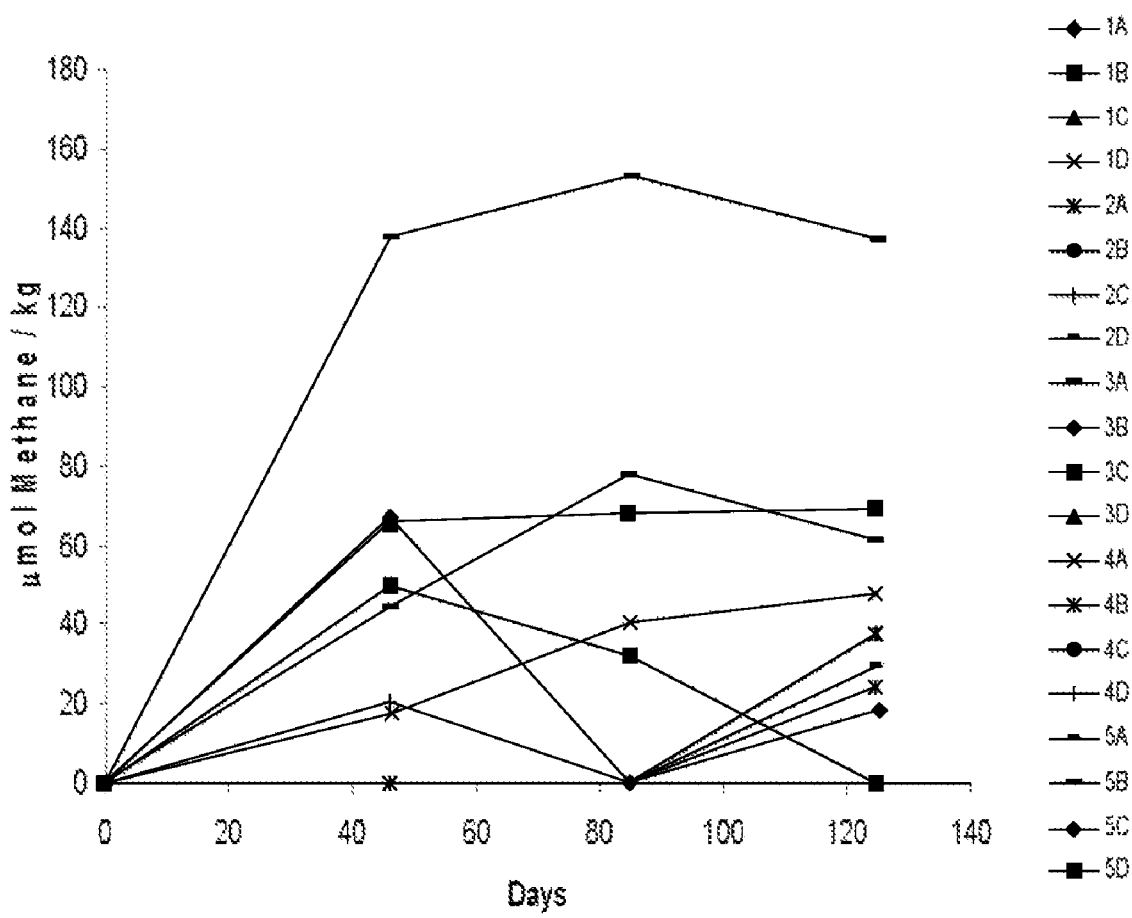
FIG. 15A shows an example of data for methane production from oil shale cores (fractured and unfractured) with various enhancements in accordance with some embodiments of the present invention.
Figure 15B:
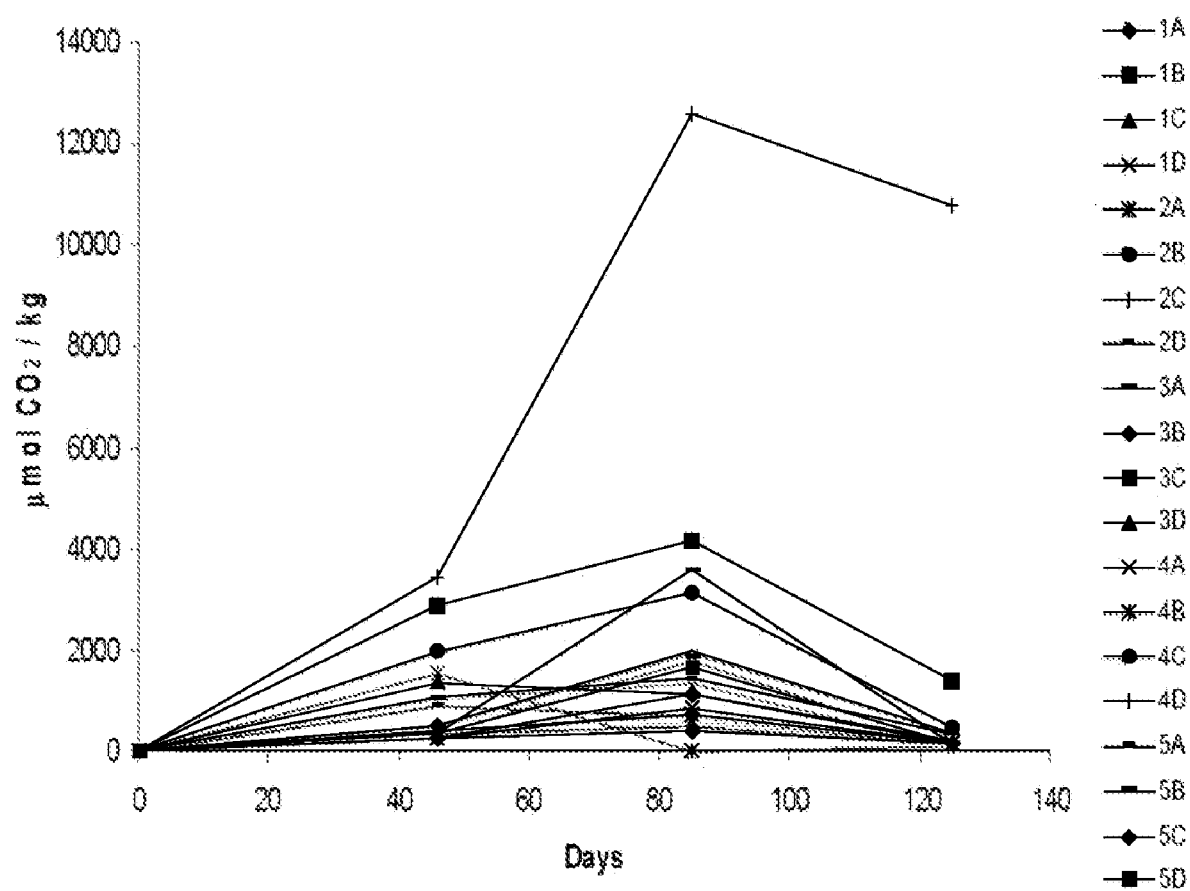
FIG. 15B shows an example of data for carbon dioxide production from oil shale cores (fractured and unfractured) with various enhancements in accordance with some embodiments of the present invention.

Oil shale used in the previous tests was cored to a diameter of 10.16 cm. These cores were fractured using a Soiltest Mechanical Soil Compactor Model CN-4235 (Lake Bluff, Ill.). The soil compactor drops a 4.54 kg shaft, 0.45 m at 2.12 m/s. Reactors were separated and grouped by fracture and treatment designation (Table 9). The treatments used in this test were chosen from those that performed the best in previous trials. Oil shale permeability and hydraulic conductivity were measured by flexible-wall parameters and were determined to be $3.09 \times 10^{-9}$ $cm^2$ and $3.41 \times 10^{-7}$ cm/s, respectively. Microbial activity is evident from the high production of carbon dioxide; however relatively small amount of methane is being produced, as shown in FIGS. 15a and 15b. Similar to the microbe studies described above, the reactors were incubated at room temperature (~20° C.). Considering the effects that incubating at 30° C. had onto those microbes, incubating the reactors at the same temperature may increase methane production.

TABLE 9

Fracture and treatment designations for the scaled-up reactors

| ID (Group) | Fracture Designation | Treatment |
|---|---|---|
| 1 | 0 Hits | |
| 2 | 15 Hits | |
| 3 | 30 Hits | |
| 4 | 45 Hits | |
| 5 | 60 Hits | |
| A | | No Amendments |
| B | | NaOH Pre-treatment |
| C | | NaOH Pre-treatment + Nutrients |
| D | | NaOH Pre-treatment + nutrients + milk |

Pre-treatment and addition of nutrients may substantially increase the rate of methane production perhaps even when exposed to temperatures where the oil-shale and water were collected (~30° C. in this case). The pre-treatment may extract the carbon source (hydrocarbons in this case) from the solid and makes it more bioavailable for microbial degradation and transformation. The adjustment of temperature to the level found where the shale was collected is optimal for microbial (methanogenic) activity. The microbe studies with coal, lignite, peat, and diesel-contaminated soil did not involve pre-treatments, which may have limited the availability of the carbon. Also, the microbes were incubated at room temperature (~20° C.), which may not have been the optimal (natural) temperature for methanogenic activity.

As can be easily understood from the foregoing, the basic concepts of the present invention may be embodied in a variety of ways. It involves both methane production techniques as well as devices to accomplish the appropriate methane system. In this application, the methane production techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims included herein or in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "injector" should be understood to encompass disclosure of the act of "injecting"—whether explicitly discussed or not—and, conversely, were there effectively disclosure of the act of "injecting", such a disclosure should be understood to encompass disclosure of an "injector" and even a "means for injecting." Such changes and alternative terms are to be understood to be explicitly included in the description.

Any patents, publications, or other references mentioned in this application for patent are hereby incorporated by reference. Any applications or patents claimed under priority in this or any subsequent applications are also hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the table below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the methane production devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claims or concepts presented.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of producing biogenic methane comprising the steps of:
   providing a hydrocarbon-bearing formation environment having a hydrocarbon-bearing formation and at least one microbial population;
   pretreating said hydrocarbon-bearing formation environment having said hydrocarbon-bearing formation and said at least one microbial population with a basic amendment;
   increasing a pH of said hydrocarbon-bearing formation environment with said basic amendment to provide a basic hydrocarbon-bearing formation environment;
   extracting at least some hydrocarbons from said hydrocarbon-bearing formation in said basic hydrocarbon-bearing formation environment;
   adjusting said pH of said basic hydrocarbon-bearing formation environment;
   microbially consuming said at least some of said hydrocarbons extracted from said hydrocarbon-bearing formation by said at least one microbial population to provide a stimulated microbial population;
   generating methane from said stimulated microbial population; and
   collecting said methane.

2. A method of producing biogenic methane according to claim 1 wherein said hydrocarbon-bearing formation is selected from a group consisting of coal, oil shale, lignite, peat, diesel-contaminated soil, coal seam, oil formations, tar sands, waste coal, petroleum sludge, drill cuttings, hydrocarbon-contaminated soil, and coal derivatives.

3. A method of producing biogenic methane according to claim 1 wherein said step of extracting said at least some hydrocarbons from said hydrocarbon-bearing formation in said basic hydrocarbon-bearing formation environment comprises the step of modifying organic matters within said hydrocarbon-bearing formation environment with said basic amendment.

4. A method of producing biogenic methane according to claim 1 wherein said step of pretreating said hydrocarbon-bearing formation environment having said hydrocarbon-bearing formation and said at least one microbial population with said basic amendment comprises the step of chemically modifying said hydrocarbons of said hydrocarbon-bearing formation with said basic amendment.

5. A method of producing biogenic methane according to claim 1 wherein said hydrocarbon-bearing formation environment is selected from a group consisting of an in-situ hydrocarbon-bearing formation environment and an ex-situ hydrocarbon-bearing environment.

6. A method of producing biogenic methane according to claim 1 and further comprising the steps of:
   removing said at least some hydrocarbons extracted from an in-situ environment;
   placing said at least some hydrocarbons in an ex-situ environment; and
   producing methane in said ex-situ environment.

7. A method of producing biogenic methane according to claim 1 wherein said step of generating said methane from said stimulated microbial population comprises the step of generating said methane from said hydrocarbons in a bioreactor.

8. A method of producing biogenic methane according to claim 1 wherein said basic hydrocarbon-bearing formation environment has a pH selected from a group consisting of up to about 10 pH, up to about 13 pH, and between about 10 pH and about 13 pH.

9. A method of producing biogenic methane according to claim 1 wherein said step of pretreating said hydrocarbon-bearing formation environment having said hydrocarbon-bearing formation and said at least one microbial population with said basic amendment comprises the step of pretreating said hydrocarbon-bearing formation environment with said basic amendment for a period of time selected from a group consisting of up to about 24 hours, up to about 48 hours, and between about 24 hours and about 48 hours.

10. A method of producing biogenic methane according to claim 1 wherein said step of adjusting said pH of said basic hydrocarbon-bearing formation environment comprises the step of adjusting said pH to a value selected from a group consisting of less than about 8 pH, less than about 9 pH, and less than about 9.8 pH.

11. A method of producing biogenic methane according to claim 1 wherein said step of adjusting said pH of said basic hydrocarbon-bearing formation environment comprises the step of neutralizing said pH of said basic hydrocarbon-bearing formation environment with an acid amendment.

12. A method of producing biogenic methane according to claim 1 wherein said basic amendment is selected from a group consisting of alkaline solutions, alkali solutions, sodium hydroxide, percarbonate, peroxide, sodium carbonate, sodium bicarbonate, hydrated sodium carbonate, nahcolite containing amendments, trona containing amendments, sodium hydroxide solutions, percarbonate solutions, peroxide solutions, sodium carbonate solutions, sodium bicarbonate solutions, hydrated sodium carbonate solutions, nahcolite containing amendment solutions, trona containing amendment solutions, and any combination thereof.

13. A method of producing biogenic methane according to claim 1 and further comprising the step of increasing a rate of methane production.

14. A method of producing biogenic methane according to claim 1 and further comprising the step of reducing an amount of carbon dioxide generated from said stimulated microbial population.

15. A method of producing biogenic methane according to claim 1 and further comprising the step of adding a microbial population stimulation amendment after said step of adjusting said pH of said basic hydrocarbon-bearing formation environment.

16. A method of producing biogenic methane according to claim 15 wherein said microbial population stimulation amendment is selected from a group consisting of corn syrup, emulsified oil, lactate, fresh milk, spoiled milk, milk, returned milk, nitrogen, phosphorous, vitamins, organic carbon, biotin, folic acid, pyrodoxine hydrochloride, thiamine hydrochloride, riboflavin, nicotinic acid, DL-calcium panthenate, vitamin B12, p-aminobenzoic acid, lipoic acid, biowastes, salts, micronutrients, surfactants, acids, bases, oxidants, acetic acid, and any combination thereof.

17. A method of producing biogenic methane according to claim 1 wherein said step of providing said hydrocarbon-bearing formation environment having said hydrocarbon-bearing formation and said at least one microbial population comprises the step of providing said hydrocarbon-bearing formation environment having said hydrocarbon-bearing formation and at least one indigenous microbial population.

18. A method of producing biogenic methane according to claim 1 and further comprising the step of injecting recycled water carrying at least one microbial population into said hydrocarbon-bearing formation environment.

19. A method of producing biogenic methane according to claim 18 wherein said recycled water is selected from a group consisting of produced water, groundwater, water from coal bed methane production, water, coal bed methane co-produced water, local groundwater, wastewater, coal produced water, reused water, amended water, amended produced water, injected water, well water, sterile water, live water, and any combination thereof.

20. A biogenic methane production system comprising:
a hydrocarbon-bearing formation environment having a hydrocarbon-bearing formation and at least one microbial population;
a basic pretreatment amendment capable of increasing a pH of said hydrocarbon-bearing formation environment to form a basic hydrocarbon-bearing formation environment and capable of extracting at least some hydrocarbons from said hydrocarbon-bearing formation;
a pH adjuster of said basic hydrocarbon-bearing formation environment;
biogenically generated methane in said hydrocarbon-bearing formation environment derived from said at least one microbial population; and
a methane collection element.

21. A biogenic methane production system according to claim 20 wherein said hydrocarbon-bearing formation is selected from a group consisting of coal, oil shale, lignite, peat, diesel-contaminated soil, coal seam, oil formations, tar sands, waste coal, petroleum sludge, drill cuttings, hydrocarbon-contaminated soil, and coal derivatives.

22. A biogenic methane production system according to claim 20 wherein said hydrocarbon-bearing formation environment is selected from a group consisting of an in-situ hydrocarbon-bearing formation environment and an ex-situ hydrocarbon-bearing environment.

23. A biogenic methane production system according to claim 20 and further comprising a bioreactor.

24. A biogenic methane production system according to claim 20 wherein said basic hydrocarbon-bearing formation environment has a pH selected from a group consisting of up to about 10 pH, up to about 13 pH, and between about 10 pH and about 13 pH.

25. A biogenic methane production system according to claim 20 wherein said basic pretreatment amendment is applied to said hydrocarbon-bearing formation environment for a period of time selected from a group consisting of up to about 24 hours, up to about 48 hours, and between about 24 hours and about 48 hours.

26. A biogenic methane production system according to claim 20 wherein said pH adjuster of said basic hydrocarbon-bearing formation environment is capable of adjusting said pH to a value selected from a group consisting of less then about 8 pH, less than about 9 pH, and less than about 9.8 pH.

27. A biogenic methane production system according to claim 20 wherein said pH adjuster comprises an acid amendment.

28. A biogenic methane production system according to claim 20 wherein said basic pretreatment amendment is selected from a group consisting of alkaline solutions, alkali solutions, sodium hydroxide, percarbonate, peroxide, sodium carbonate, sodium bicarbonate, hydrated sodium carbonate, nahcolite containing amendments, trona containing amendments, sodium hydroxide solutions, percarbonate solutions, peroxide solutions, sodium carbonate solutions, sodium bicarbonate solutions, hydrated sodium carbonate solutions, nahcolite containing amendment solutions, trona containing amendment solutions, and any combination thereof.

29. A biogenic methane production system according to claim 20 and further comprising a microbial population stimulation amendment.

30. A biogenic methane production system according to claim 29 wherein said microbial population stimulation amendment is selected from a group consisting of corn syrup, emulsified oil, lactate, fresh milk, spoiled milk, milk, returned milk, nitrogen, phosphorous, vitamins, organic carbon, biotin, folic acid, pyrodoxine hydrochloride, thiamine hydrochloride, riboflavin, nicotinic acid, DL-calcium panthenate, vitamin B12, p-aminobenzoic acid, lipoic acid, biowastes, salts, micronutrients, surfactants, acids, bases, oxidants, acetic acid, and any combination thereof.

31. A biogenic methane production system according to claim 20 wherein said at least one microbial population comprises at least one indigenous microbial population.

* * * * *